US011624792B2

(12) United States Patent
Stickle et al.

(10) Patent No.: US 11,624,792 B2
(45) Date of Patent: *Apr. 11, 2023

(54) RADIO FREQUENCY HEAD COIL FOR A MAGNETIC RESONANCE IMAGING SYSTEM AND METHODS THEREOF

(71) Applicant: General Electric Company, Schenectady, NY (US)

(72) Inventors: Yun-Jeong Stickle, Solon, OH (US); Balint Franko, Aurora, OH (US); Sarah Tenley, Cleveland Heights, OH (US); Clyve Konrad Rosales Follante, Twinsburg, OH (US); Patrick Quarterman, Long Beach, NY (US); Nabeel Malik, Solon, OH (US)

(73) Assignee: General Electric Company, Schenectady, NY (US)

(*) Notice: Subject to any disclaimer, the term of this patent is extended or adjusted under 35 U.S.C. 154(b) by 487 days.

This patent is subject to a terminal disclaimer.

(21) Appl. No.: 16/463,589

(22) PCT Filed: Jul. 21, 2017

(86) PCT No.: PCT/US2017/043191
§ 371 (c)(1),
(2) Date: May 23, 2019

(87) PCT Pub. No.: WO2018/097860
PCT Pub. Date: May 31, 2018

(65) Prior Publication Data
US 2019/0277927 A1    Sep. 12, 2019

Related U.S. Application Data

(60) Provisional application No. 62/426,364, filed on Nov. 25, 2016.

(51) Int. Cl.
*G01R 33/34* (2006.01)
*G01R 33/3415* (2006.01)
(Continued)

(52) U.S. Cl.
CPC ...... *G01R 33/34084* (2013.01); *A61B 5/0042* (2013.01); *A61B 5/055* (2013.01);
(Continued)

(58) Field of Classification Search
CPC .......................... G01R 33/24; G01R 33/34084
See application file for complete search history.

(56) References Cited

U.S. PATENT DOCUMENTS 4,621,237 A    11/1986 Timms
4,712,067 A *  12/1987 Roschmann ..... G01R 33/34046
                                                     324/318
(Continued)

OTHER PUBLICATIONS

Keil et al., "A64-Channel 3T Array Coil for Accelerated Brain MRI" Magnetic Resonance in Medicine 70:248-258 (2013) (Year: 2013).*

(Continued)

*Primary Examiner* — Colin T. Sakamoto

(57) ABSTRACT

A radio frequency head coil for a magnetic resonance imaging system is provided. The radio frequency head coil includes a body operative to be disposed on a head of a patient, and an extended lip disposed on the body and operative to receive a magnetic resonance signal. At least some of the magnetic resonance signal is emitted by a region of the patient disposed between a brain stem of the patient up to and including a vertebra of the patient.

28 Claims, 24 Drawing Sheets

(51) Int. Cl.
*A61B 5/055* (2006.01)
*A61B 5/00* (2006.01)
*G01R 33/28* (2006.01)
*G01R 33/36* (2006.01)
*A61B 5/318* (2021.01)

(52) U.S. Cl.
CPC ..... *G01R 33/283* (2013.01); *G01R 33/34007* (2013.01); *G01R 33/3415* (2013.01); *A61B 5/318* (2021.01); *G01R 33/3657* (2013.01)

(56) References Cited

U.S. PATENT DOCUMENTS

| | | | |
|---|---|---|---|
| 4,825,162 A | | 4/1989 | Roemer |
| 4,897,604 A | * | 1/1990 | Carlson ............ G01R 33/34084 324/318 |
| 5,136,244 A | * | 8/1992 | Jones ................. G01R 33/3628 324/318 |
| 5,166,618 A | * | 11/1992 | Jones ............... G01R 33/34069 324/318 |
| 5,221,902 A | * | 6/1993 | Jones ............... G01R 33/34084 324/318 |
| 5,435,302 A | | 7/1995 | Lenkinski |
| 5,682,098 A | | 10/1997 | Vij |
| 5,905,378 A | | 5/1999 | Giaquinto |
| 6,084,411 A | | 7/2000 | Giaquinto |
| 6,501,980 B1 | | 12/2002 | Carlon |
| 6,650,926 B1 | | 11/2003 | Chan |
| 6,836,117 B2 | | 12/2004 | Mitsuru |
| 6,980,000 B2 | | 12/2005 | Wong |
| 7,177,671 B2 | | 2/2007 | Nabetani |
| 7,212,002 B2 | | 5/2007 | Greim |
| 7,450,984 B2 | | 11/2008 | Engelhard |
| 7,619,416 B2 | | 11/2009 | Nordmeyer-Massner |
| 7,945,308 B2 | | 5/2011 | Tropp |
| 8,046,046 B2 | | 10/2011 | Chan |
| 8,179,136 B2 | | 5/2012 | Chan |
| 8,207,736 B2 | | 6/2012 | Chu |
| 8,269,498 B2 | | 9/2012 | Zhang |
| 8,362,776 B2 | | 1/2013 | Chu |
| 8,441,258 B2 | | 5/2013 | Chan |
| 8,487,620 B2 | | 7/2013 | Brown |
| 8,598,880 B2 | | 12/2013 | Dalveren |
| 8,624,597 B2 | | 1/2014 | Banerjee |
| 9,000,766 B2 | | 4/2015 | Chu |
| 9,002,431 B2 | | 4/2015 | Jones |
| 9,678,180 B2 | | 6/2017 | Yang |
| 10,827,948 B1 | * | 11/2020 | Tramm ................ A61B 5/7405 |
| 2005/0007116 A1 | | 1/2005 | Davis |
| 2005/0107686 A1 | * | 5/2005 | Chan .................. G01R 33/3415 600/422 |
| 2007/0270683 A1 | * | 11/2007 | Meloy .................. A61G 13/121 5/601 |
| 2008/0204021 A1 | | 8/2008 | Leussler |
| 2013/0320981 A1 | | 12/2013 | Bulumulla |
| 2014/0210466 A1 | | 7/2014 | Arias |
| 2015/0065852 A1 | * | 3/2015 | Driemel ................ A61B 5/055 600/410 |
| 2015/0115962 A1 | * | 4/2015 | Culver ............. G01R 33/34084 29/605 |
| 2015/0173678 A1 | | 6/2015 | Jones |

OTHER PUBLICATIONS

Fuentes et al. "Micro-Electromechanical Systems (MEMS) based RF-switches in MRI—a performance study." Proceedings of the 18th Annual Meeting of ISMRM, Stockholm, Sweden. 2010 (Year: 2010).*

Balthazar Lechene, et al; High quality printed receive coils for clothing integration, PowerPoint presentation; ISMRM 24th Annual Meeting & Exhibition, May 7-13, 2016; Singapore; 20 pages.

Bei Zhang, et al; High Impedance Detector Arrays for Magnetic Resonance; arXiv: 1709.03416v1 [physics.ins-det] Sep. 11, 2017; 16 pages.

Joseph R. Corea, et al; Screen-printed flexible MRI receive coils; Nature Communications, 7:10839, DOI:10.1038/ncomms10839, www.nature.com/naturecommunications; Mar. 10, 2016; 7 pages.

* cited by examiner

RADIO FREQUENCY HEAD COIL FOR A MAGNETIC RESONANCE IMAGING SYSTEM AND METHODS THEREOF

CROSS-REFERENCE TO RELATED APPLICATIONS

This application claims the benefit of U.S. Provisional Application Ser. No. 62/426,364, filed on Nov. 25, 2016, which is hereby incorporated by reference in its entirety.

BACKGROUND

Technical Field

Embodiments of the invention relate generally to magnetic resonance imaging ("MRI") systems, and more specifically, to a radio frequency ("RF") head coil for a MRI system and methods thereof.

Discussion of Art

MRI is a widely accepted and commercially available technique for obtaining digitized visual images representing the internal structure of objects having substantial populations of atomic nuclei that are susceptible to nuclear magnetic resonance ("NMR") and/or ("MR"). Many MRI systems use superconductive magnets to scan a subject/patient via imposing a strong main magnetic field on the nuclei in the subject to be imaged. The nuclei are excited by a radio frequency ("RF") signal/pulse transmitted by a RF coil at characteristics NMR (Larmor) frequencies. By spatially disturbing localized magnetic fields surrounding the subject and analyzing the resulting RF responses from the nuclei as the excited protons relax back to their lower energy normal state, a map or image of these nuclei responses as a function of their spatial location is generated and displayed. An image of the nuclei responses provides a non-invasive view of a subject's internal structure.

Many MRI systems utilize RF coils to both transmit the radio frequency pulses and to receive the resulting RF responses. Many such RF coils, known as RF head coils, have shapes conforming to a human head. Many RF head coils, however, are limited in the range of possible human heads they can accommodate, i.e., there are many human heads having dimensions for which traditional RF head coils are not sized for. Further, many patients experience high levels of stress when wearing traditional RF head coil in the bore of a MRI system, as such coils usually have small eye slits that allow the patient to view only the interior of the bore. Further still, many RF head coils are made from materials that degrade, e.g., crack, when exposed to cleaning materials/chemicals, e.g., isopropyl alcohol typically used in hospitals.

What is needed, therefore, is an improved RF head coil for a MRI system and methods thereof.

BRIEF DESCRIPTION

In an embodiment, a radio frequency head coil for a magnetic resonance imaging system is provided. The radio frequency head coil includes a body operative to be disposed on a head of a patient, and an extended lip disposed on the body and operative to receive a magnetic resonance signal. At least some of the magnetic resonance signal is emitted by a region of the patient disposed between a brain stem of the patient up to and including a vertebra of the patient.

In another embodiment, a magnetic resonance imaging system is provided. The magnetic resonance imaging system includes a magnet assembly operative to stimulate a patient such that the patient emits a magnetic resonance signal. The magnetic resonance imaging system further includes a radio frequency head coil operative to be disposed on a head of the patient and having an extended lip operative to receive the magnetic resonance signal. The magnetic resonance imaging system further includes a controller in electronic communication with the radio frequency head coil and operative to generate one or more images based at least in part on the magnetic resonance signal. At least some of the magnetic resonance signal is emitted by a region of the patient disposed between a brain stem of the patient up to and including a vertebra of the patient.

In yet another embodiment, a method of magnetic resonance imaging a patient is provided. The method includes: stimulating a patient via a magnet assembly such that the patient emits a magnetic resonance signal; receiving the magnetic resonance signal via an extended lip of a radio frequency head coil disposed on a head of the patient; and generating one or more images based at least in part on the magnetic resonance signal via a controller in electronic communication with the radio frequency head coil. At least some of the magnetic resonance signal is emitted by a region of the patient disposed between a brain stem of the patient up to and including a vertebra of the patient.

DRAWINGS

The present invention will be better understood from reading the following description of non-limiting embodiments, with reference to the attached drawings, wherein below:

Figure 3:
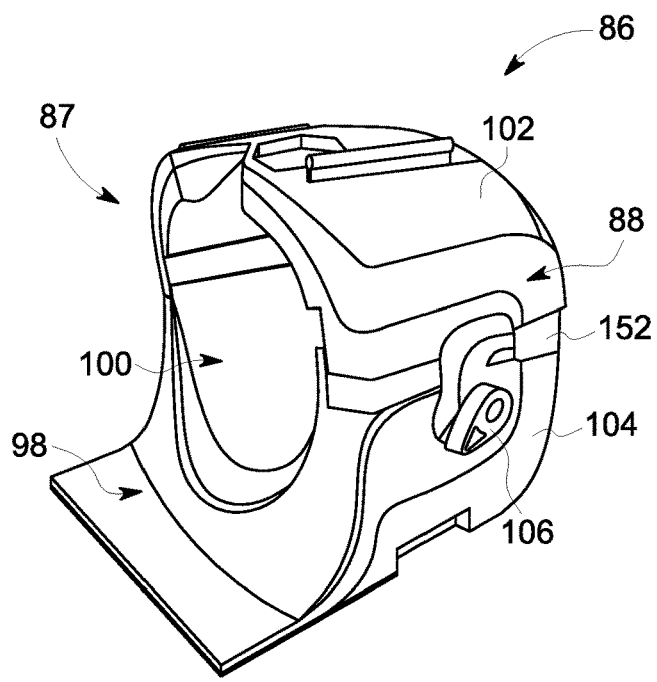
FIG. 3 is a perspective view of the front and left sides of a RF head coil of the system of FIG. 1, in accordance with an embodiment of the invention.
Figure 7:
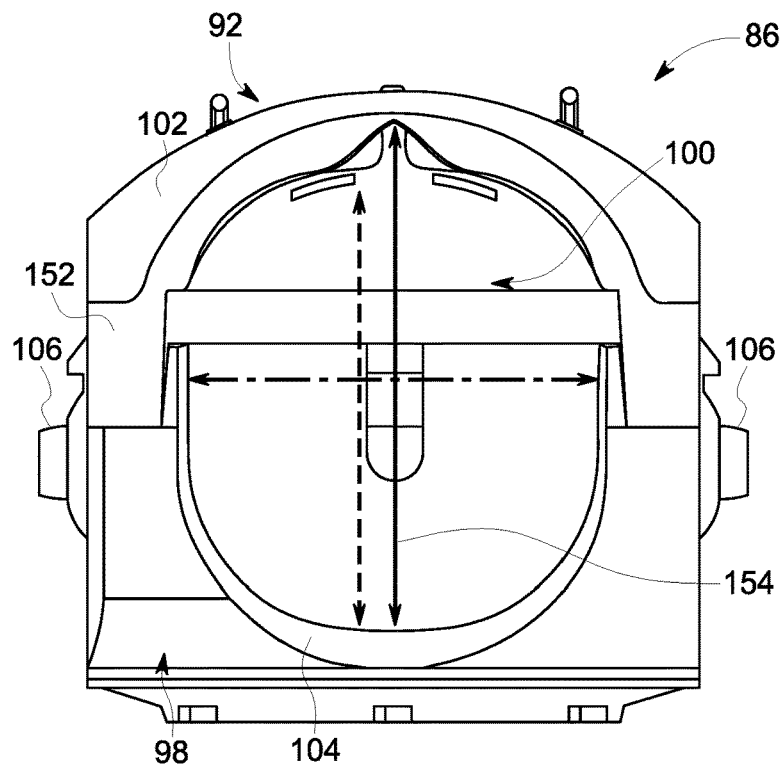
FIG. 7 is another view of the bottom side of the RF head coil of FIG. 3, wherein the RF head coil includes a spacer, in accordance with an embodiment of the invention.
Figure 8:
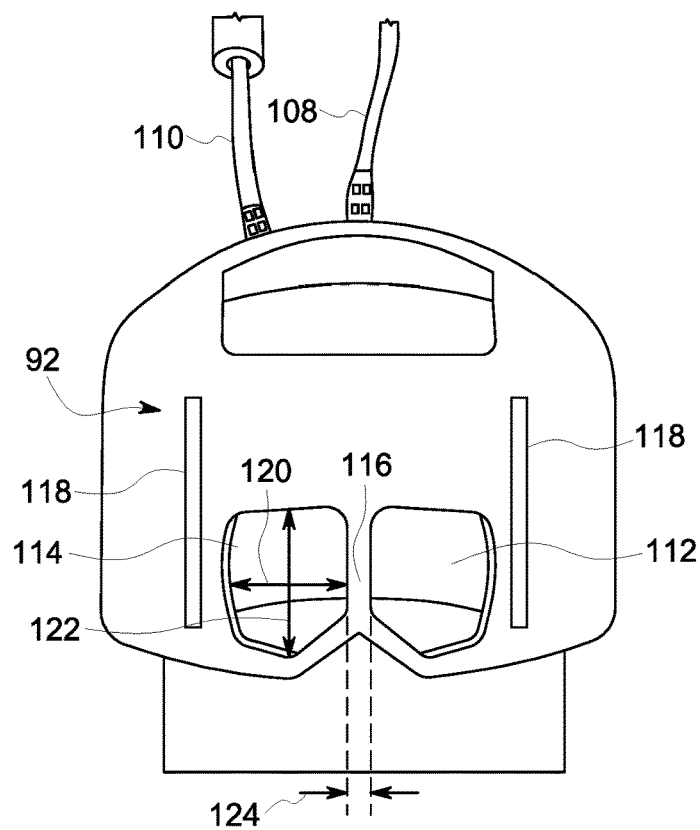
Figure 9:
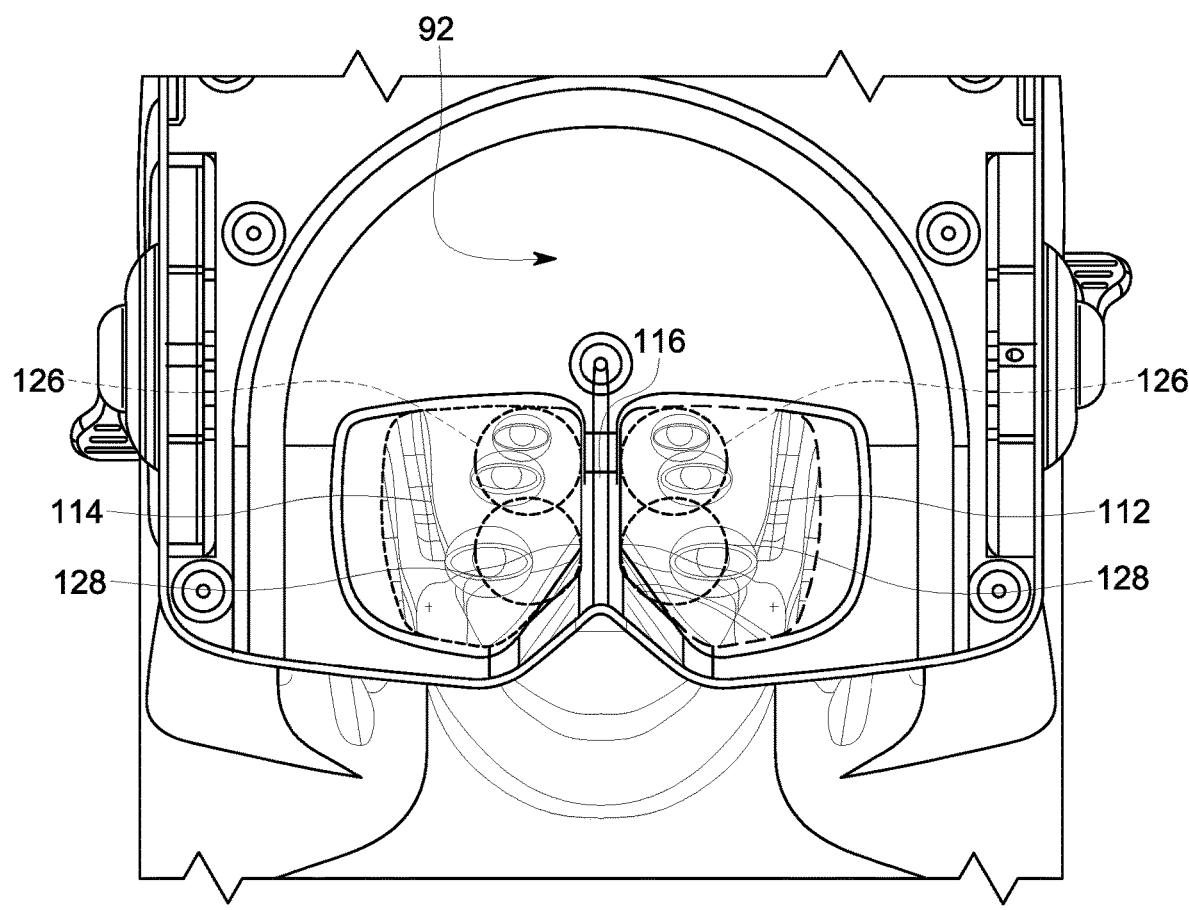
Figure 10:
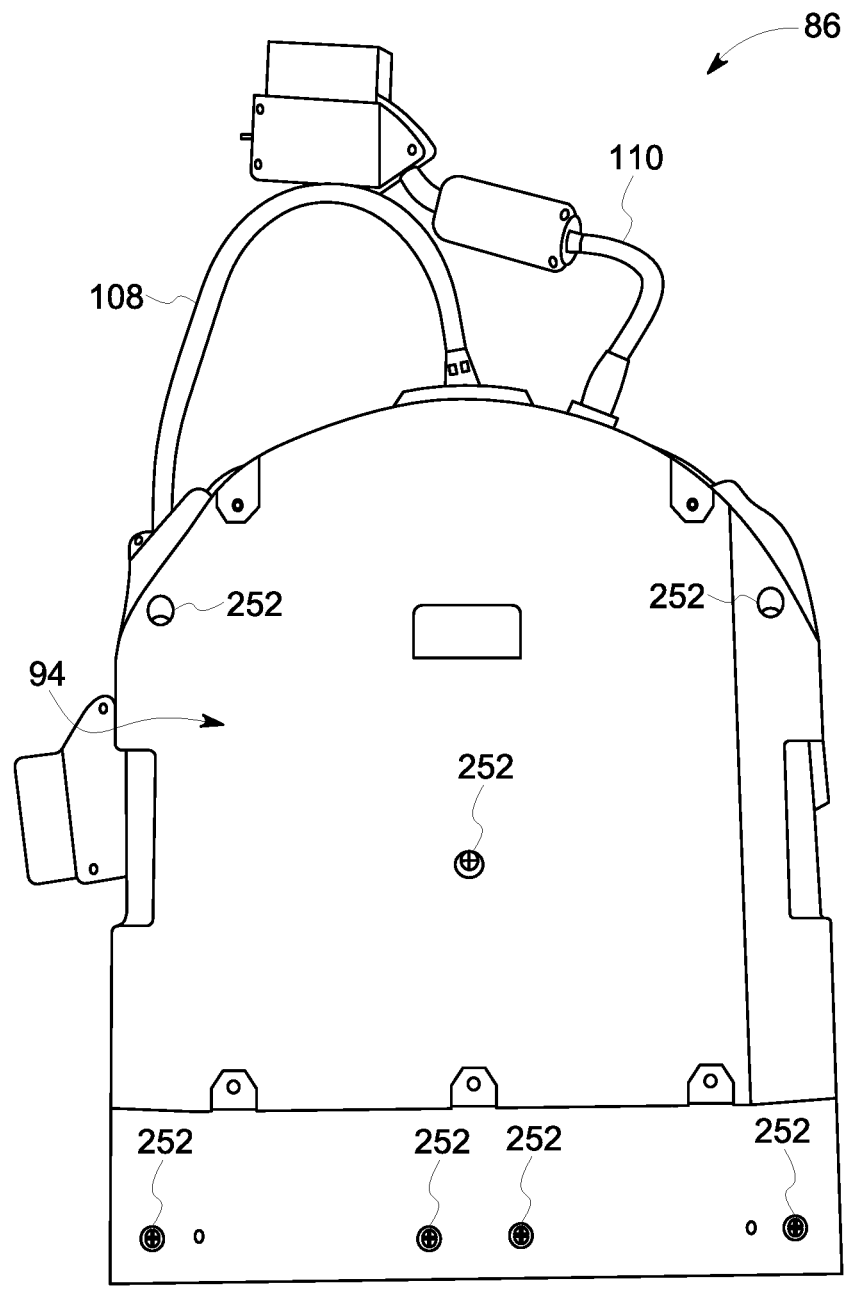
Figure 11:
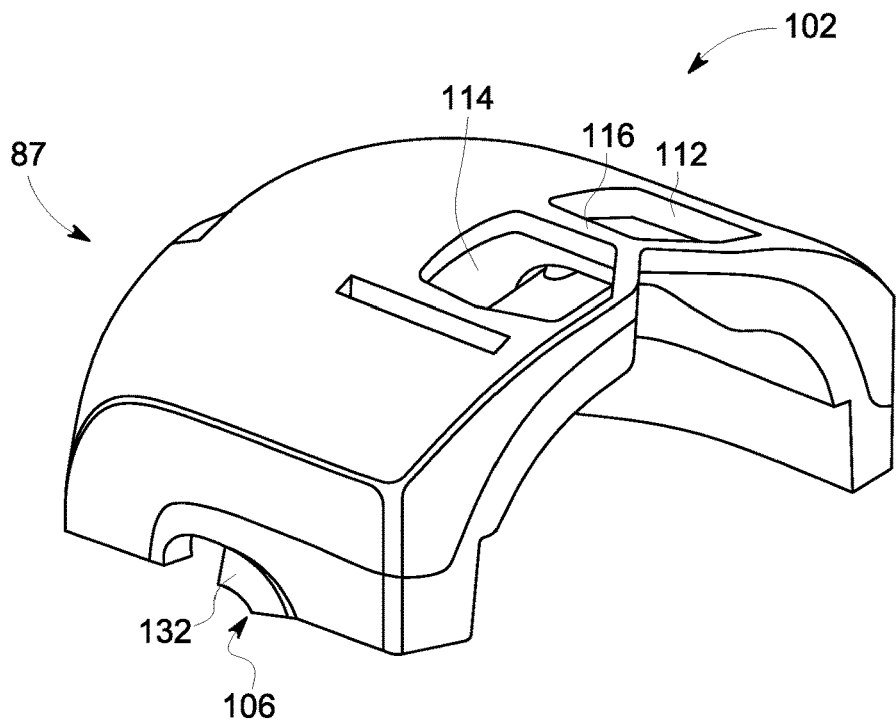
Figure 12:
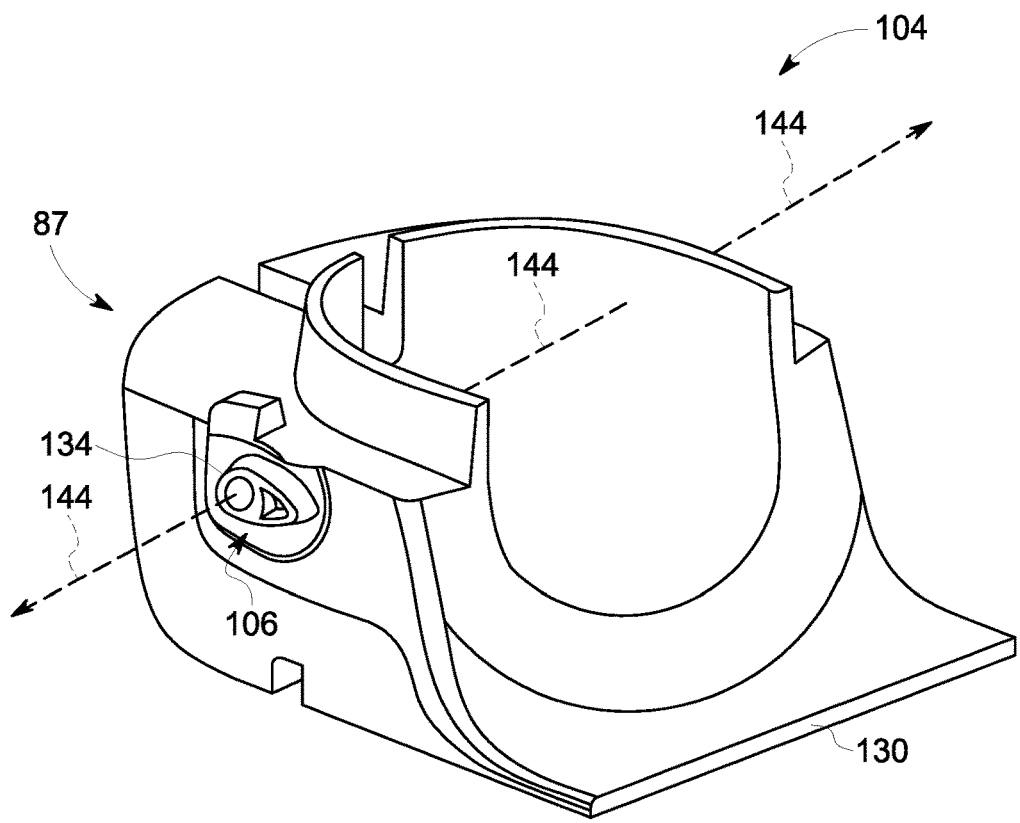
Figure 13:
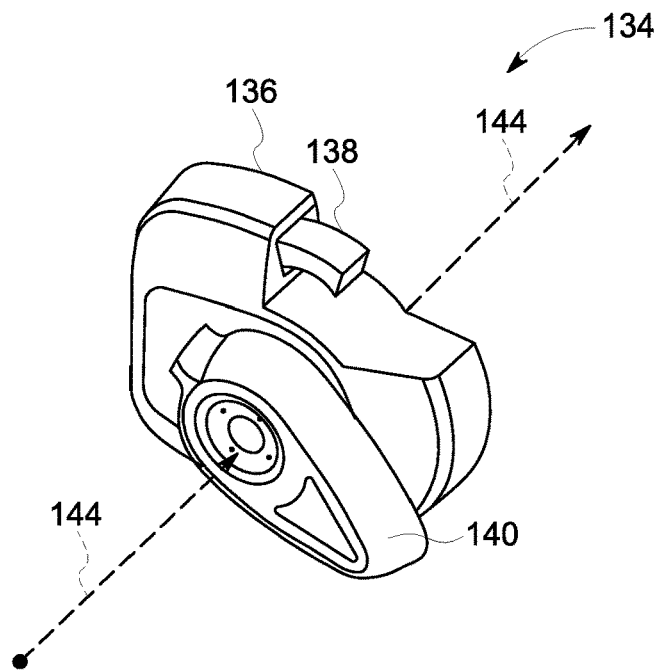
Figure 14:
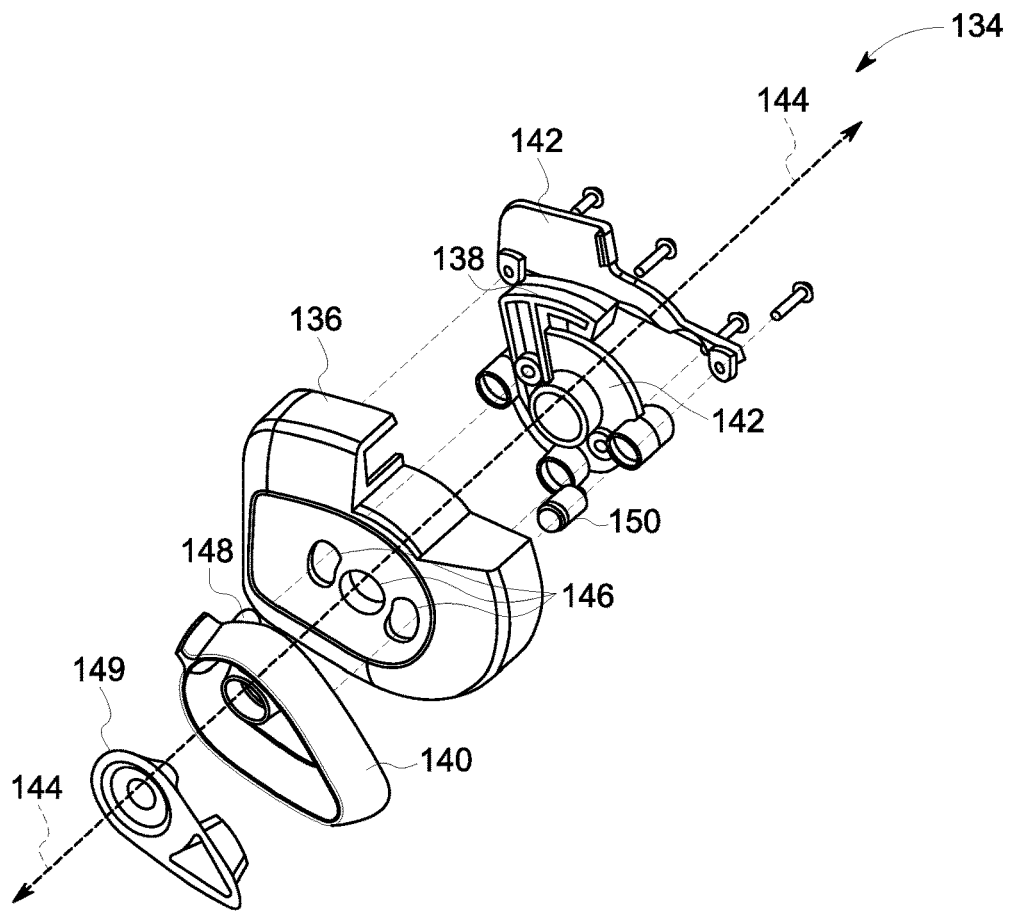
Figure 15:
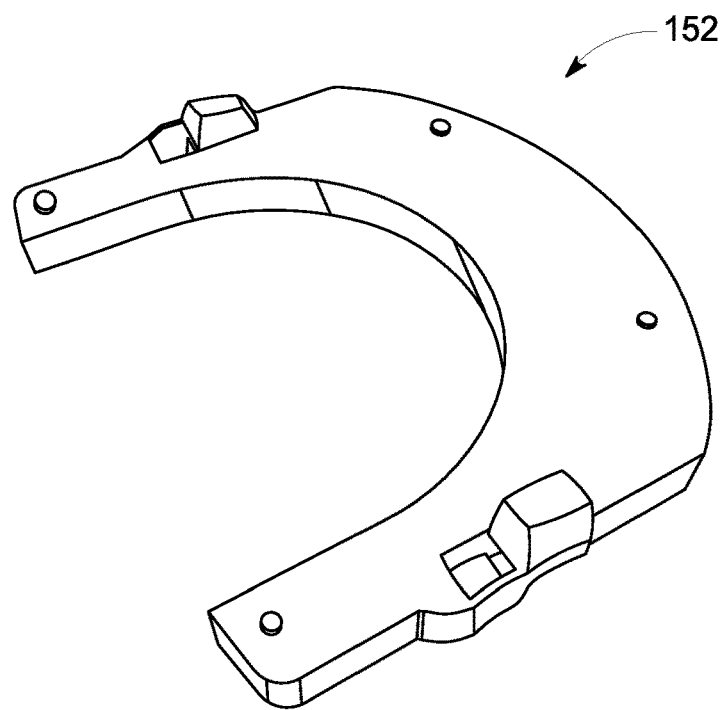
Figure 16:
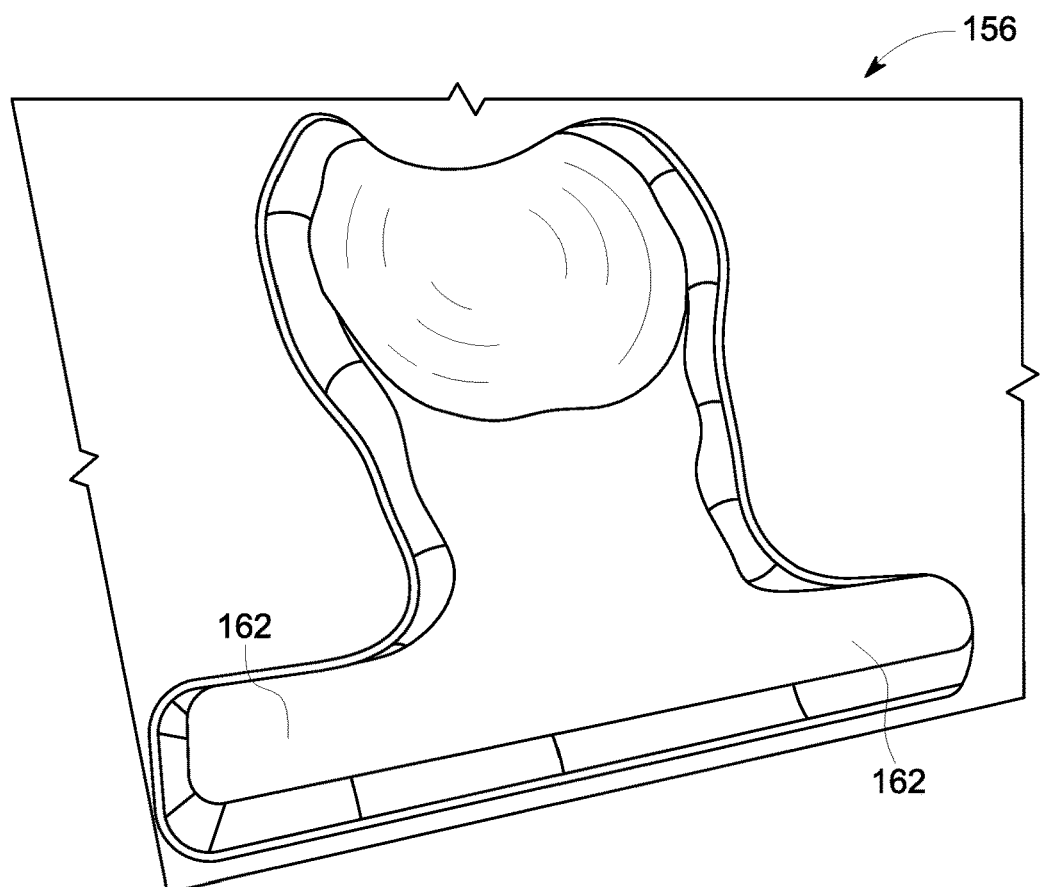
Figure 17:
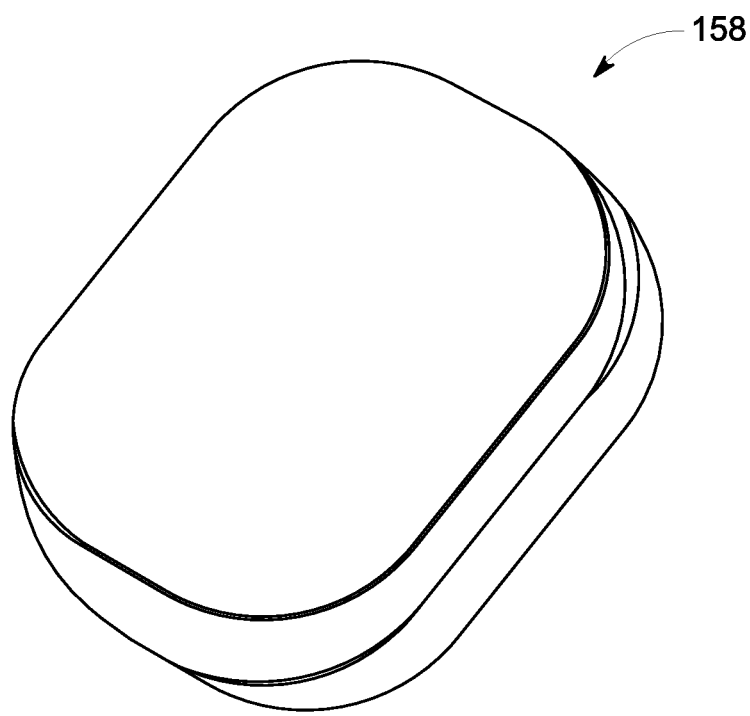
Figure 18:
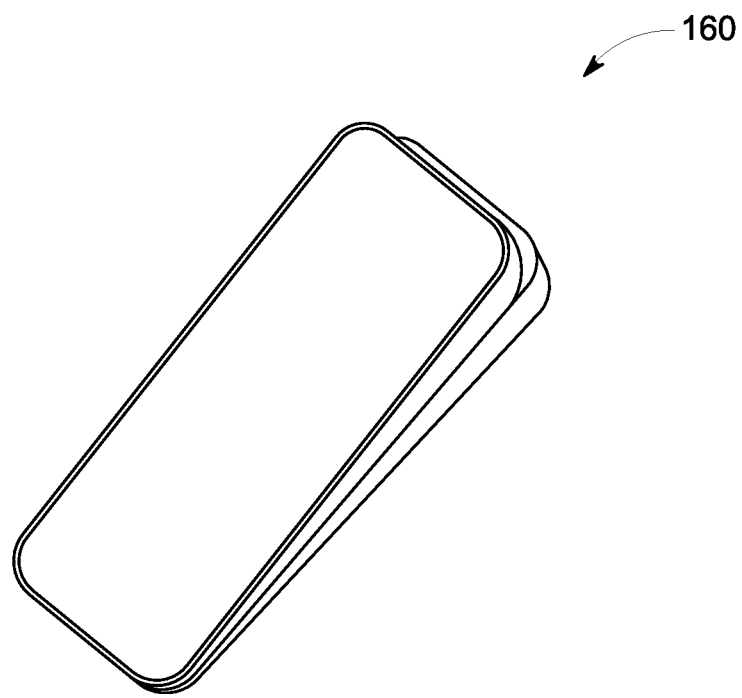
Figure 19:
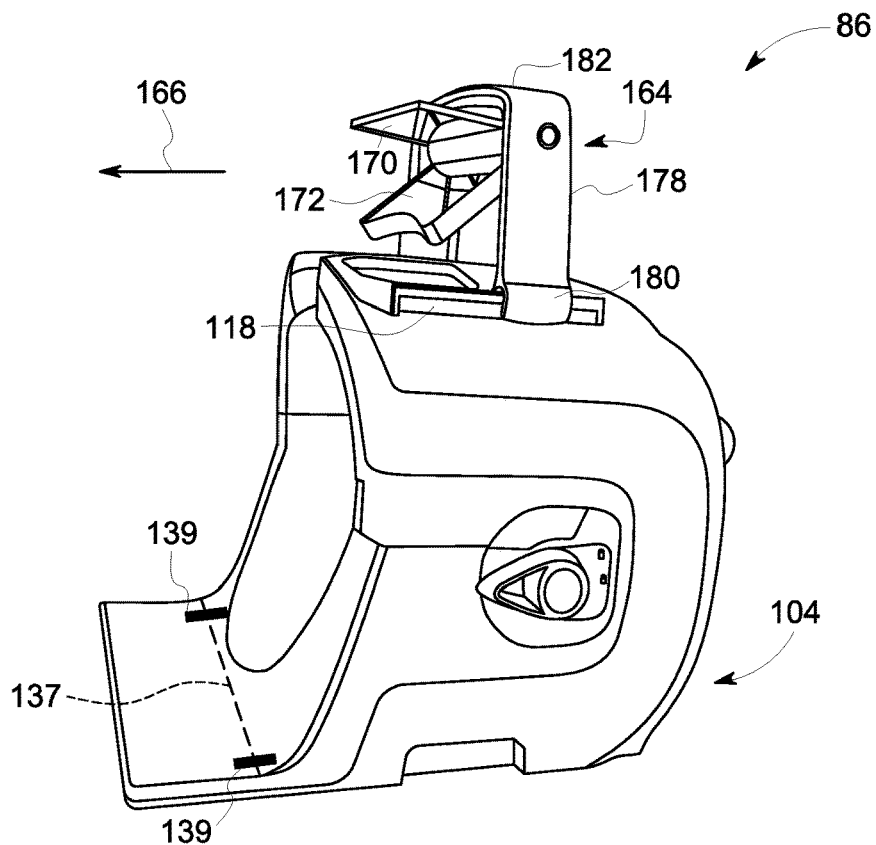
Figure 20:
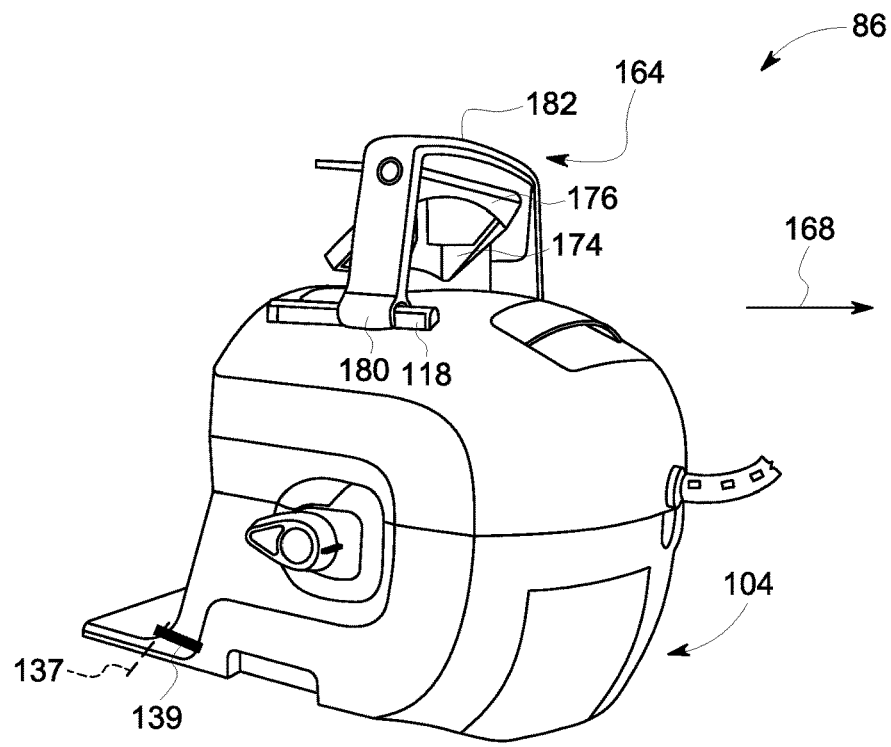
Figure 21:
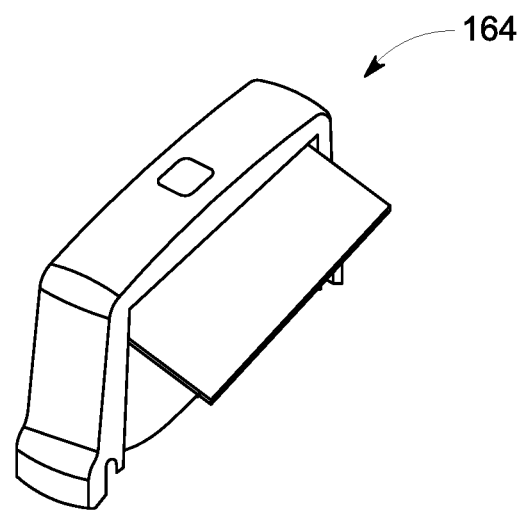
Figure 22:
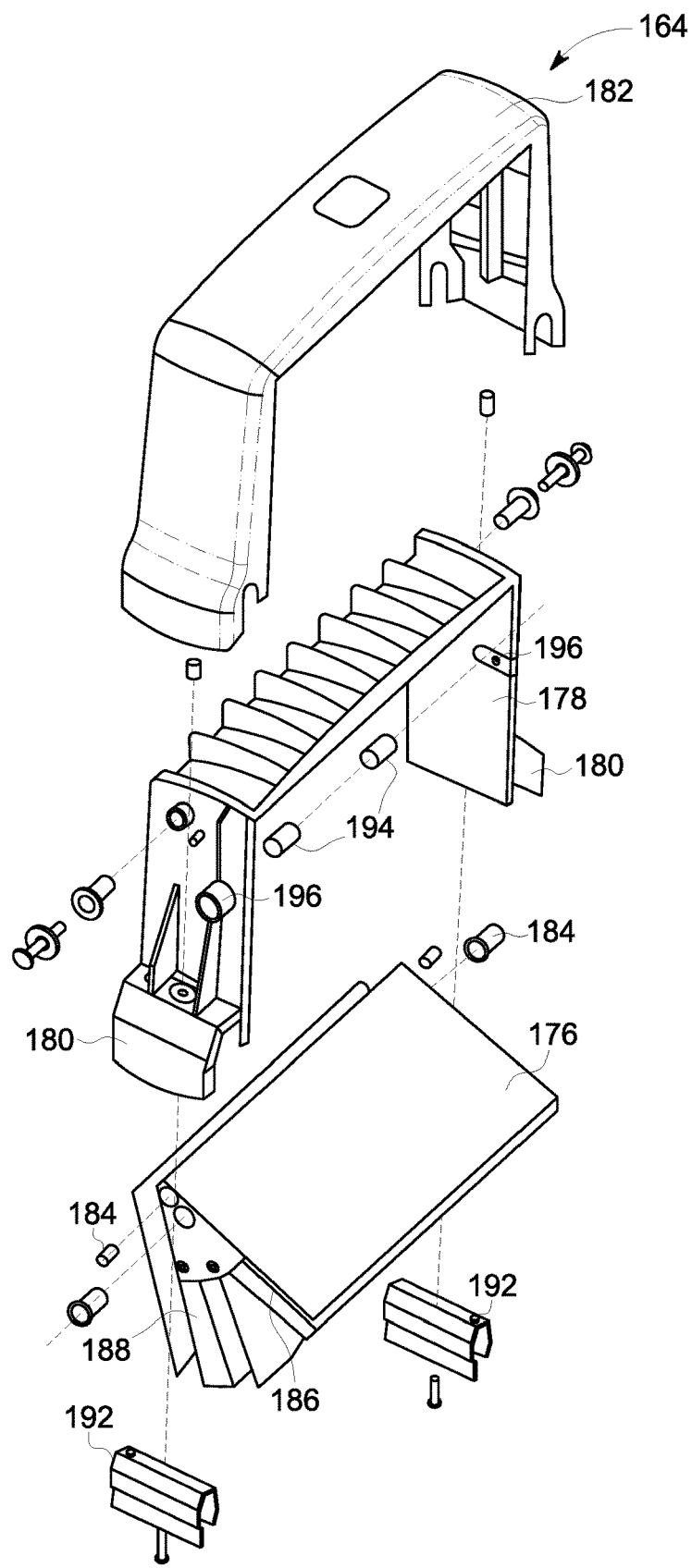
Figure 23:
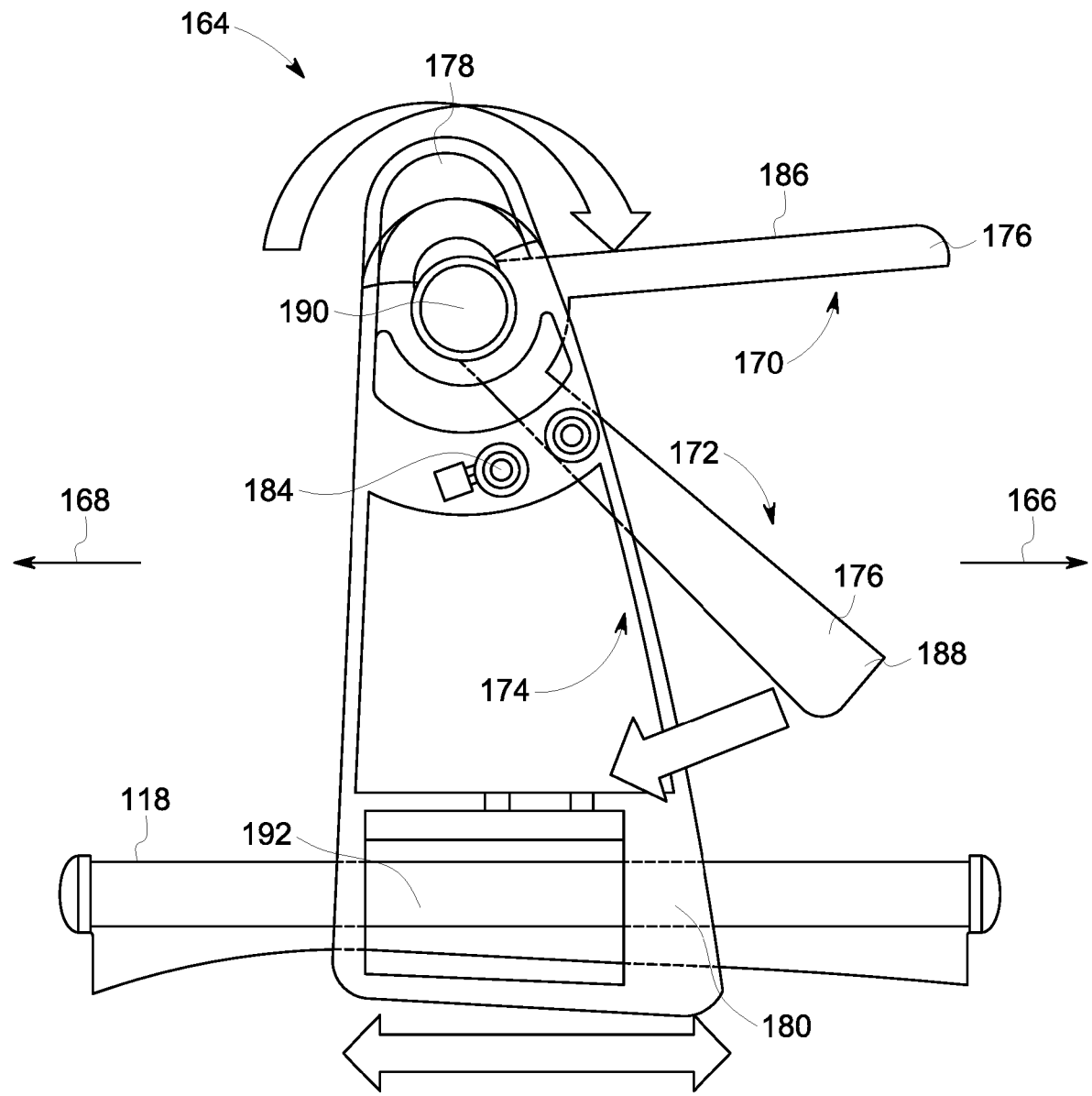
Figure 24:
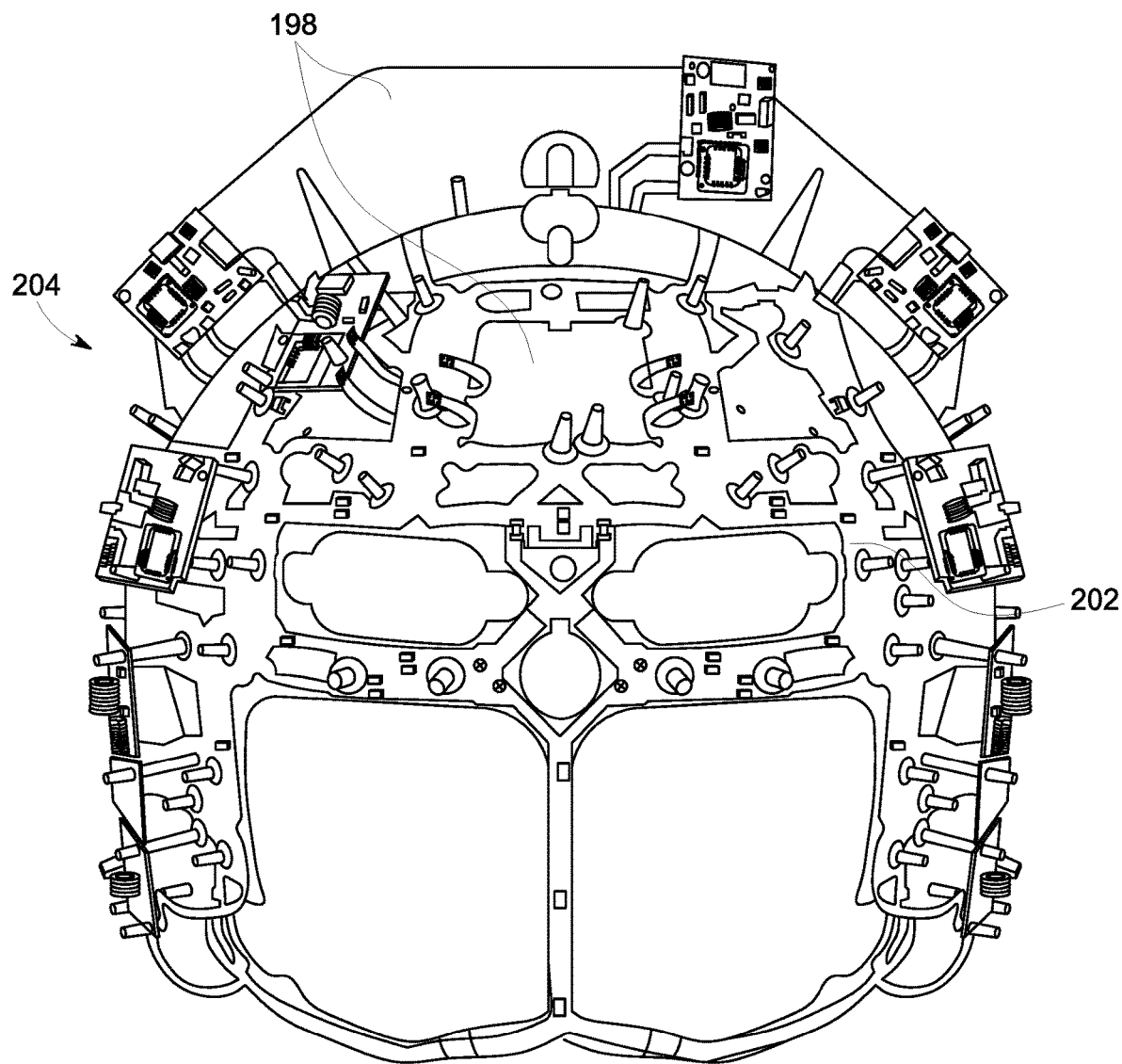
Figure 25:
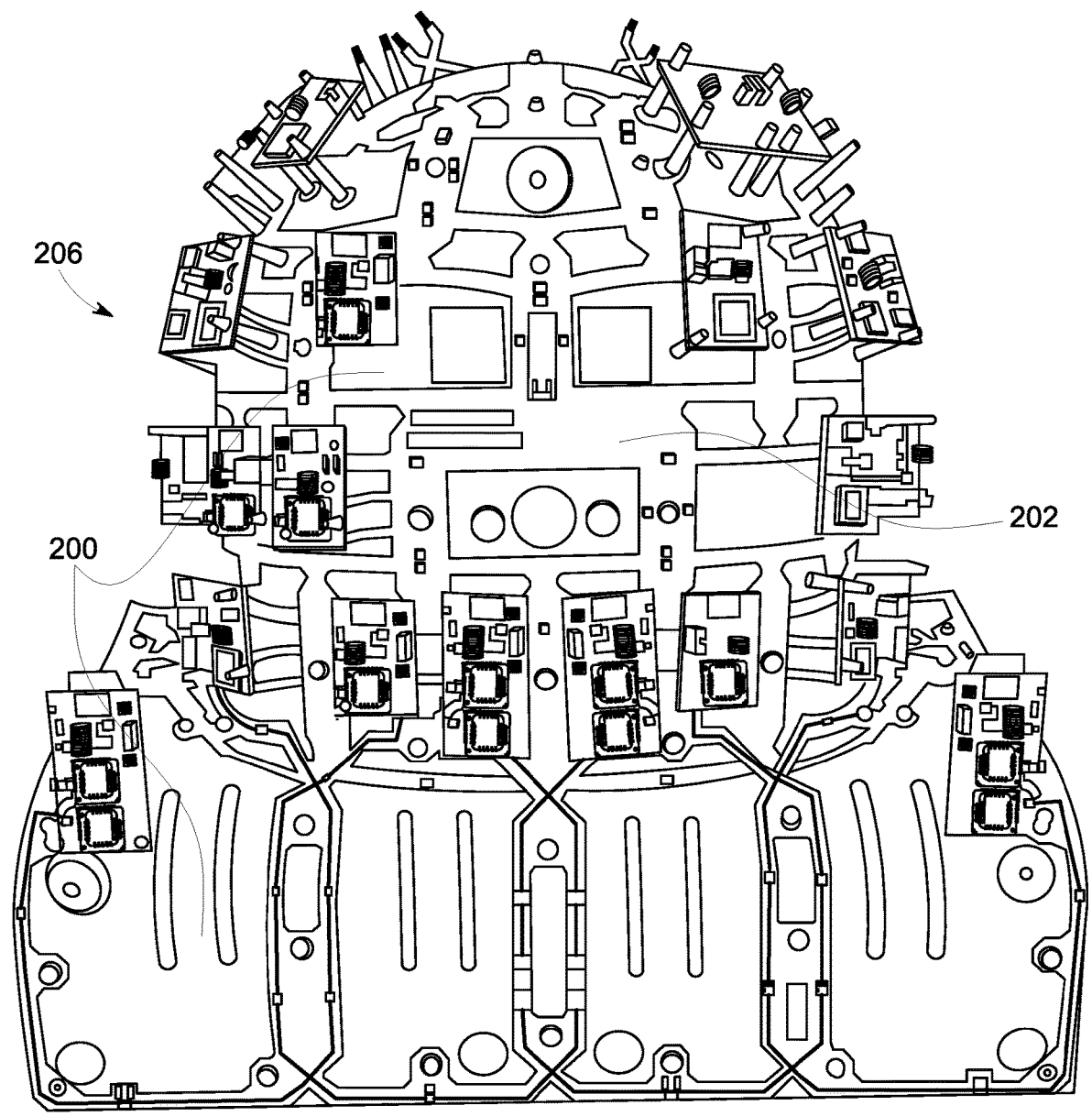
Figure 26:
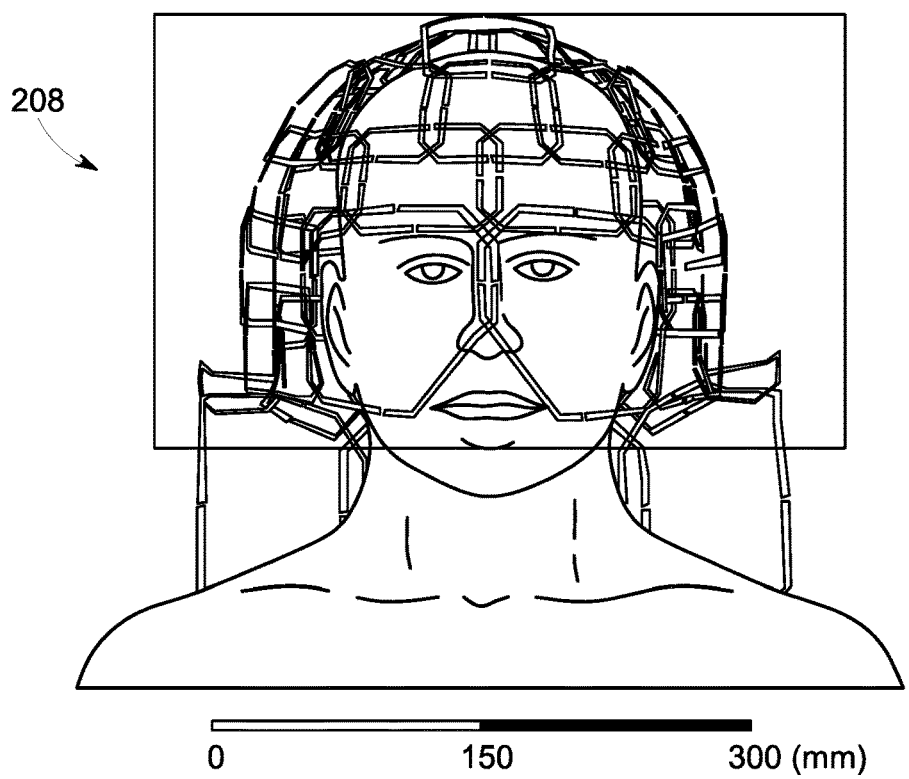
Figure 27:
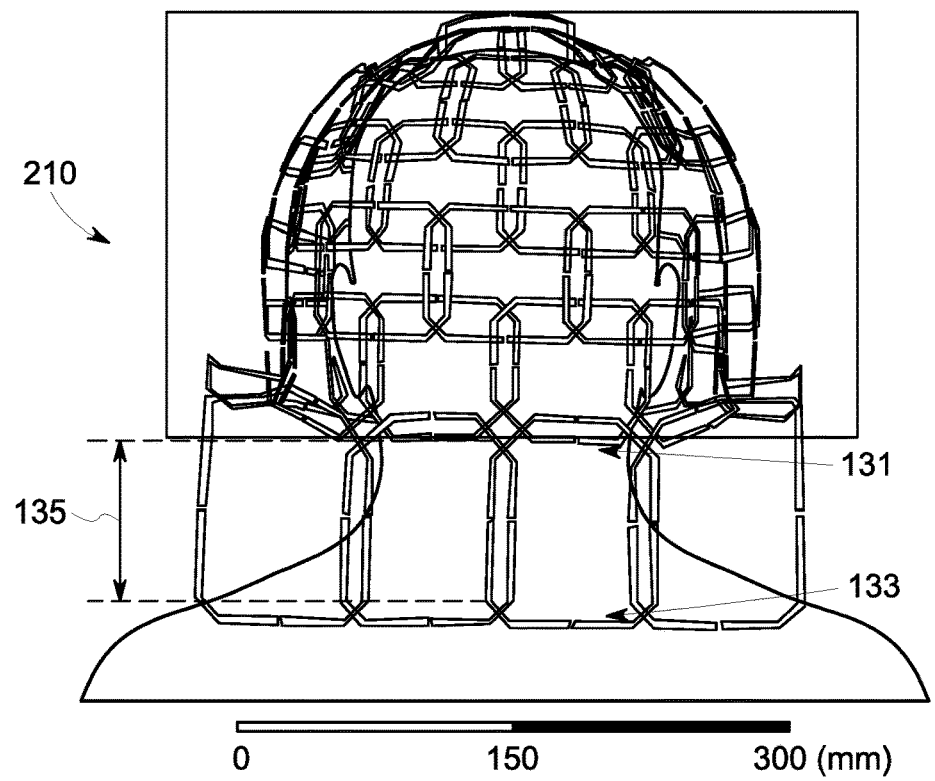
Figure 28:
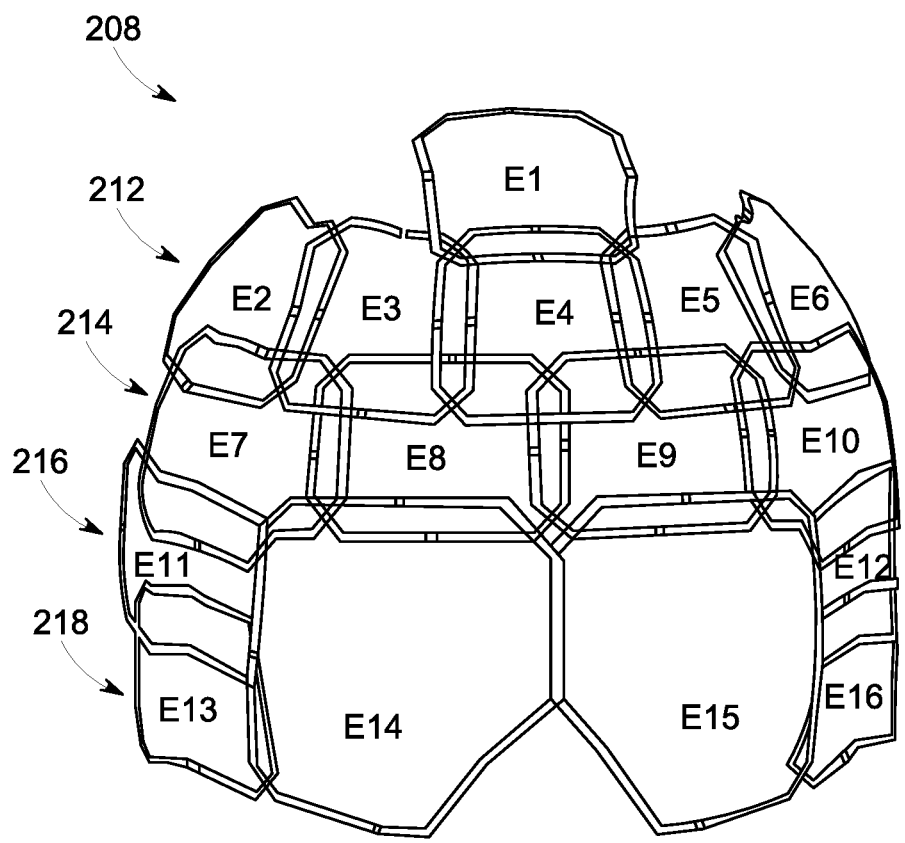
Figure 29:
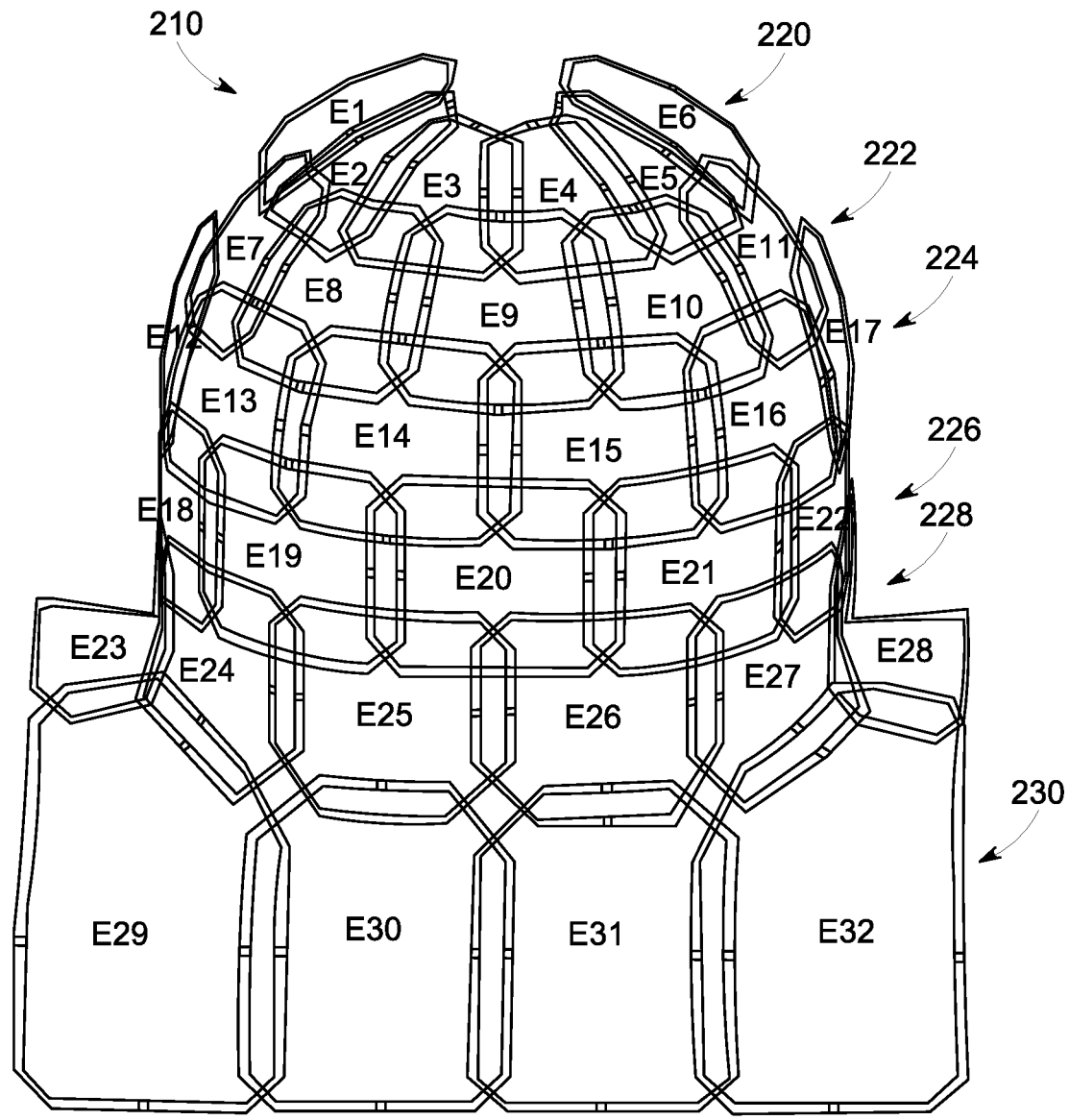
Figure 30:
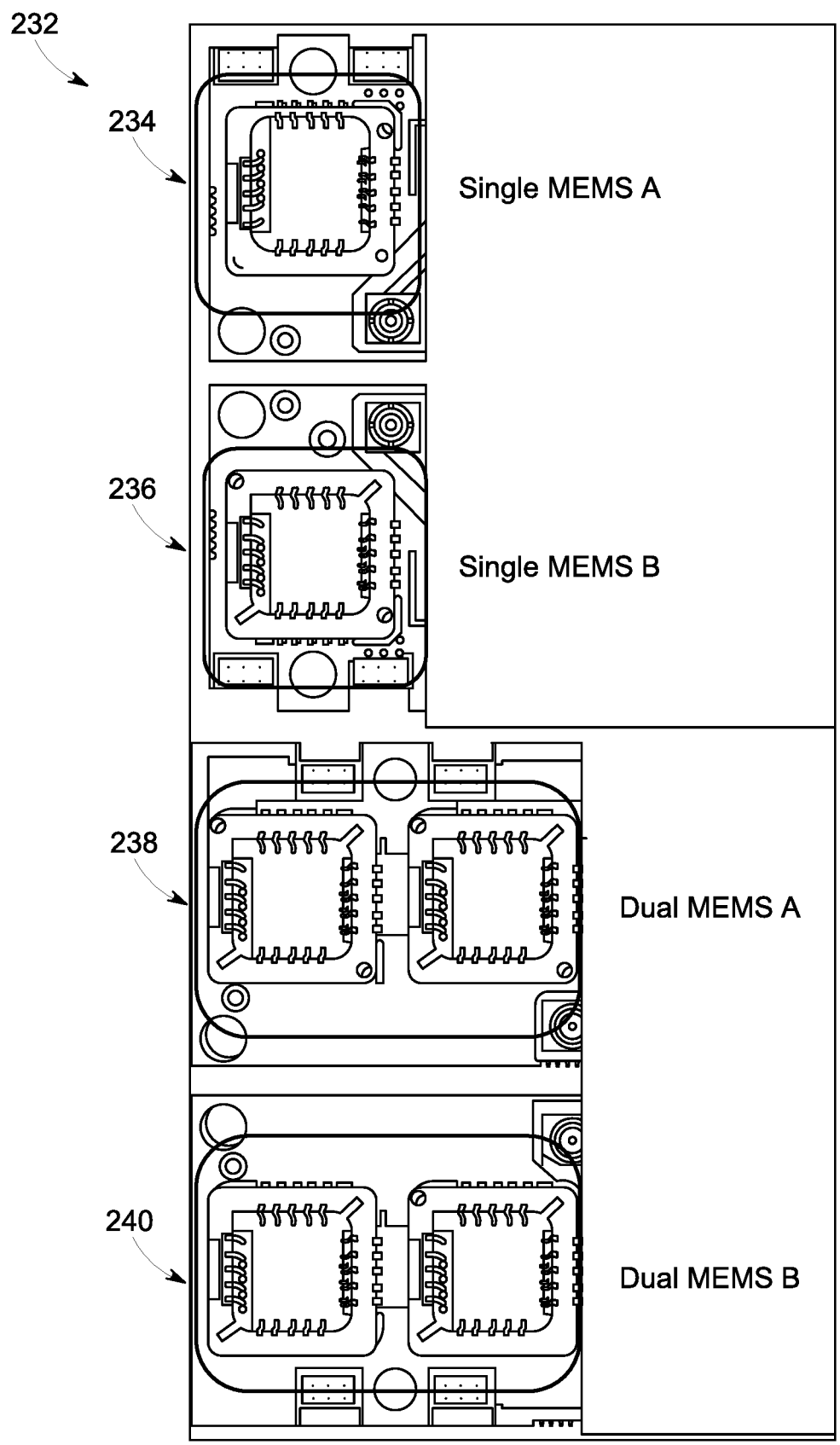
Figure 31:
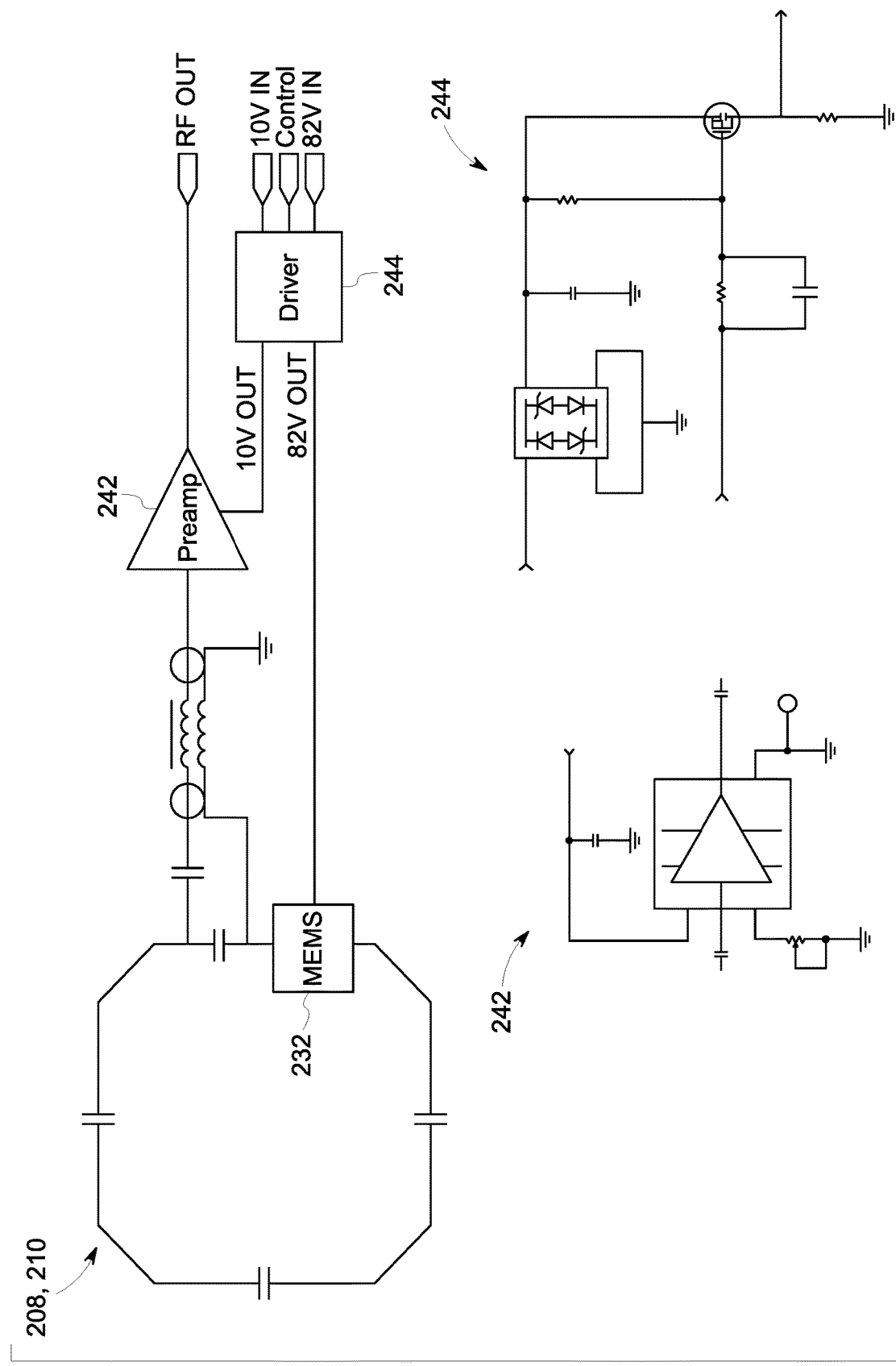
Figure 32:
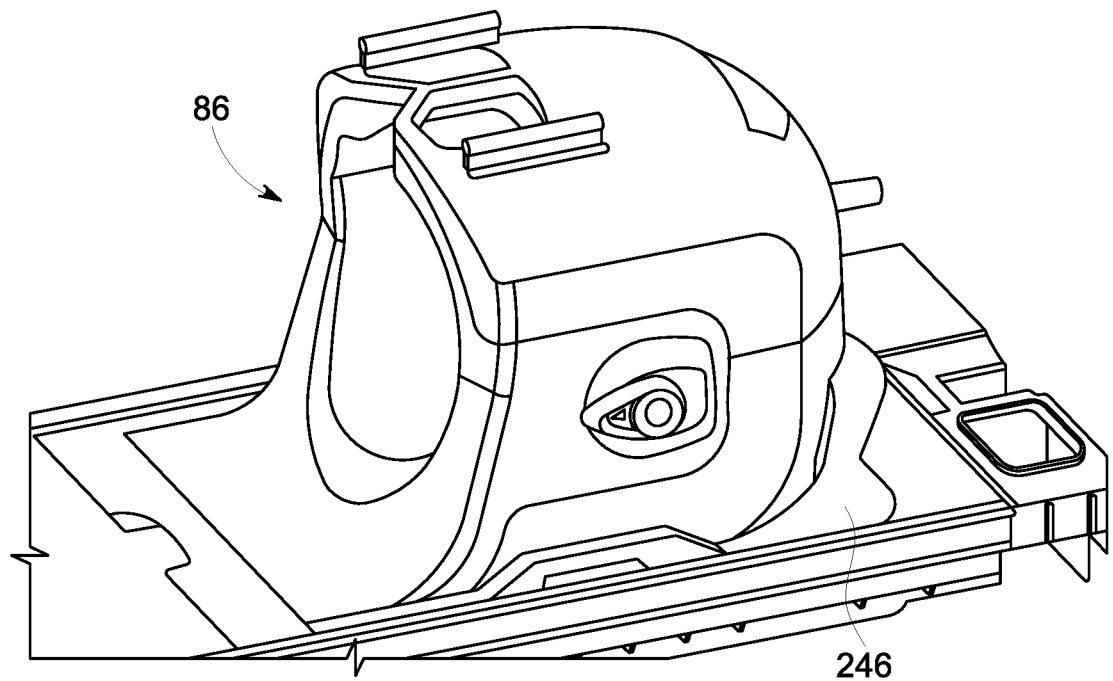
Figure 33:
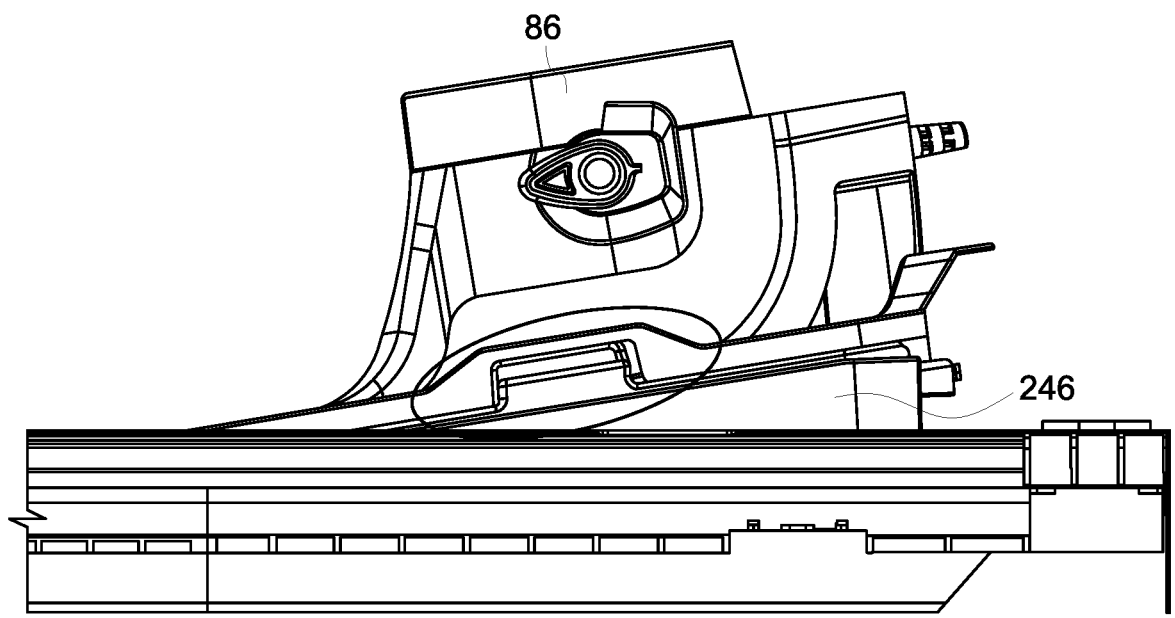
Figure 34:
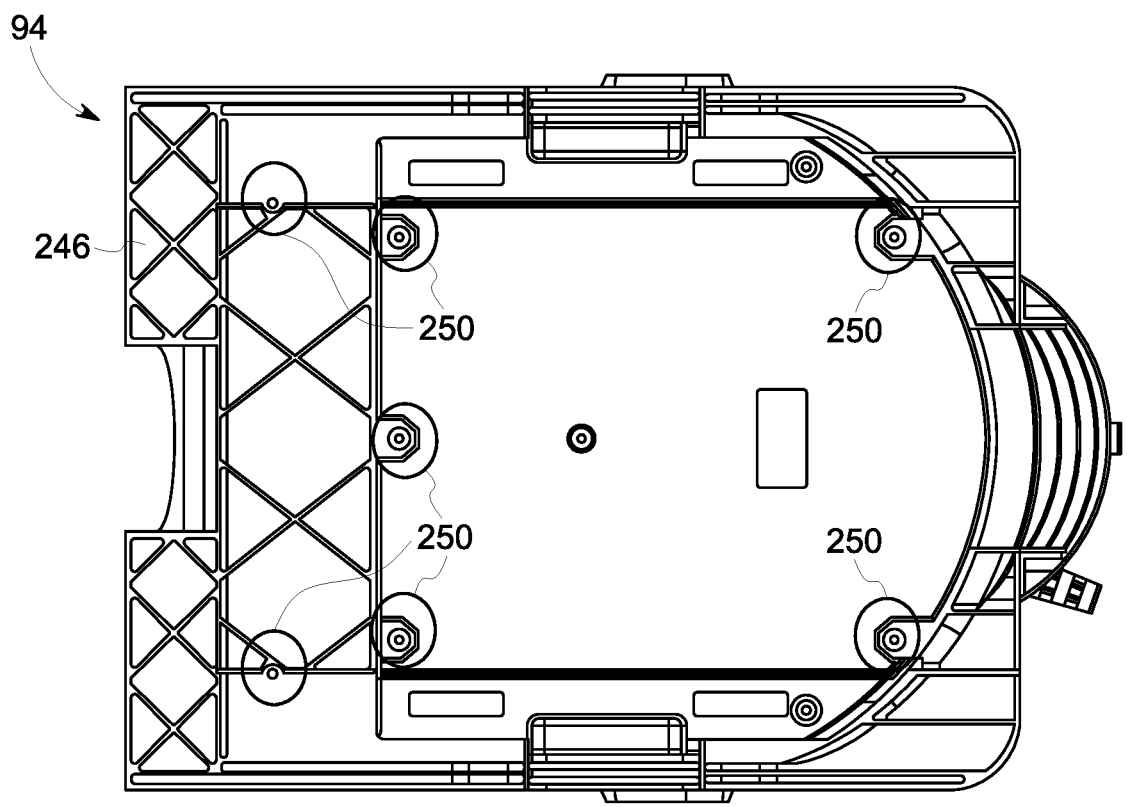
Figure 35:
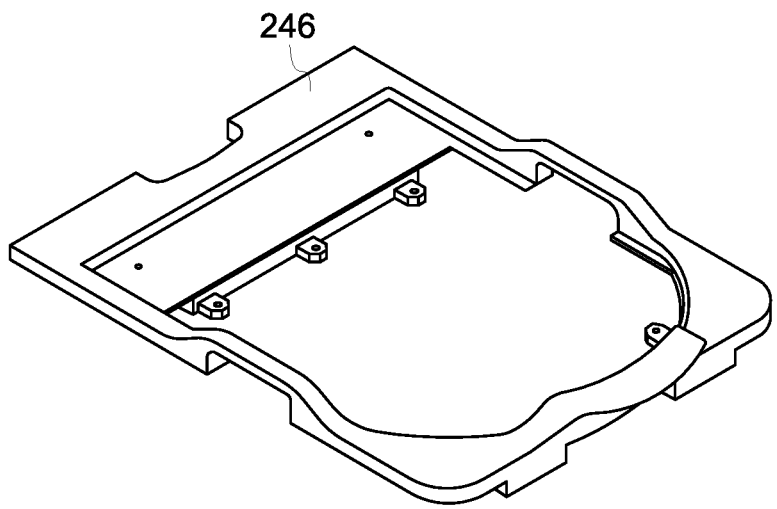

FIG. 8 view of the front side of the RF head coil of FIG. 3, in accordance with an embodiment of the invention;

FIG. 9 is another view of the front side of the RF head coil of FIG. 3, in accordance with an embodiment of the invention;

FIG. 10 is a view of the back side of the RF head coil of FIG. 3, in accordance with an embodiment of the invention;

FIG. 11 is a perspective view of an anterior portion of the RF head coil of FIG. 3, in accordance with an embodiment of the invention;

FIG. 12 is a perspective view of a posterior portion the RF head coil of FIG. 3, in accordance with an embodiment of the invention;

FIG. 13 is a perspective view of a locking mechanism of the RF head coil of FIG. 3 in accordance with an embodiment of the invention;

FIG. 14 is an exploded view of the locking mechanism of FIG. 3, in accordance with an embodiment of the invention;

FIG. 15 is a perspective vide of the spacer of FIG. 7, in accordance with an embodiment of the invention;

FIG. 16 is a perspective view of a head pad of the RF head coil of FIG. 3, in accordance with an embodiment of the invention;

FIG. 17 is a perspective view of a wedge pad of the RF head coil of FIG. 3, in accordance with an embodiment of the invention;

FIG. 18 is a perspective view of another wedge pad of the RF head coil of FIG. 3, in accordance with an embodiment of the invention;

FIG. 19 is a perspective view of the RF head coil of FIG. 3, wherein the RF head coil includes a mirror assembly and a selectively attachable extended lip, in accordance with an embodiment of the invention;

FIG. 20 is another perspective view of the RF head coil of FIG. 3, wherein the RF head coil includes the mirror assembly and the selectively attachable extended lip of FIG. 19, in accordance with an embodiment of the invention;

FIG. 21 is a perspective view of the mirror assembly of FIGS. 19 and 20, in accordance with an embodiment of the invention;

FIG. 22 is an exploded view of the mirror assembly of FIGS. 19 and 20, in accordance with an embodiment of the invention;

FIG. 23 is a diagram of the side of the mirror assembly of FIGS. 19 and 20, in accordance with an embodiment of the invention;

FIG. 24 is a view of the front of an anterior snap-fit bracket shell of the anterior portion of FIG. 11, in accordance with an embodiment of the invention;

FIG. 25 is a view of the rear of a posterior snap-fit bracket shell of the posterior portion of FIG. 12, in accordance with an embodiment of the invention;

FIG. 26 is a diagram of an anterior coil layout of the anterior portion of FIG. 11, in accordance with an embodiment of the invention;

FIG. 27 is a diagram of a posterior coil layout of the posterior portion of FIG. 11, in accordance with an embodiment of the invention;

FIG. 28 is another diagram of the anterior coil layout of FIG. 26, in accordance with an embodiment of the invention;

FIG. 29 is another diagram of the posterior coil layout of FIG. 27, in accordance with an embodiment of the invention;

FIG. 30 is a diagram of one or more micro-electromechanical ("MEM") switches of the RF head coil of FIG. 3, in accordance with an embodiment of the invention;

FIG. 31 is circuit diagram of a coil element of the RF head coil of FIG. 3, in accordance with an embodiment of the invention;

FIG. 32 is a perspective view of a table adapter of the RF head coil of FIG. 3, in accordance with an embodiment of the invention;

FIG. 33 is a view of the left side of the table adapter of FIG. 32, in accordance with an embodiment of the invention;

FIG. 34 is a view of the bottom side of the of the table adapter of FIG. 32, in accordance with an embodiment of the invention; and FIG. 35 is another perspective view of the table adapter of FIG. 32, in accordance with an embodiment of the invention.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. As used herein the terms "optical communication", "optically communicate" and "optically connected" mean that the referenced elements are able to direct, reflect, and/or receive photons between each other. Further, the term "MR signal," as used herein, refers to the cumulated value/RF wave of the RF responses from the nuclei of an object stimulated in accordance with the above outline principles of MR.

Further, while the embodiments disclosed herein are described with respect to an MRI system, it is to be understood that embodiments of the present invention may be applicable to other imaging systems. Further still, as will be appreciated, embodiments of the present invention related imaging systems may be used to analyze tissue generally and are not limited to human tissue.

Figure 1:
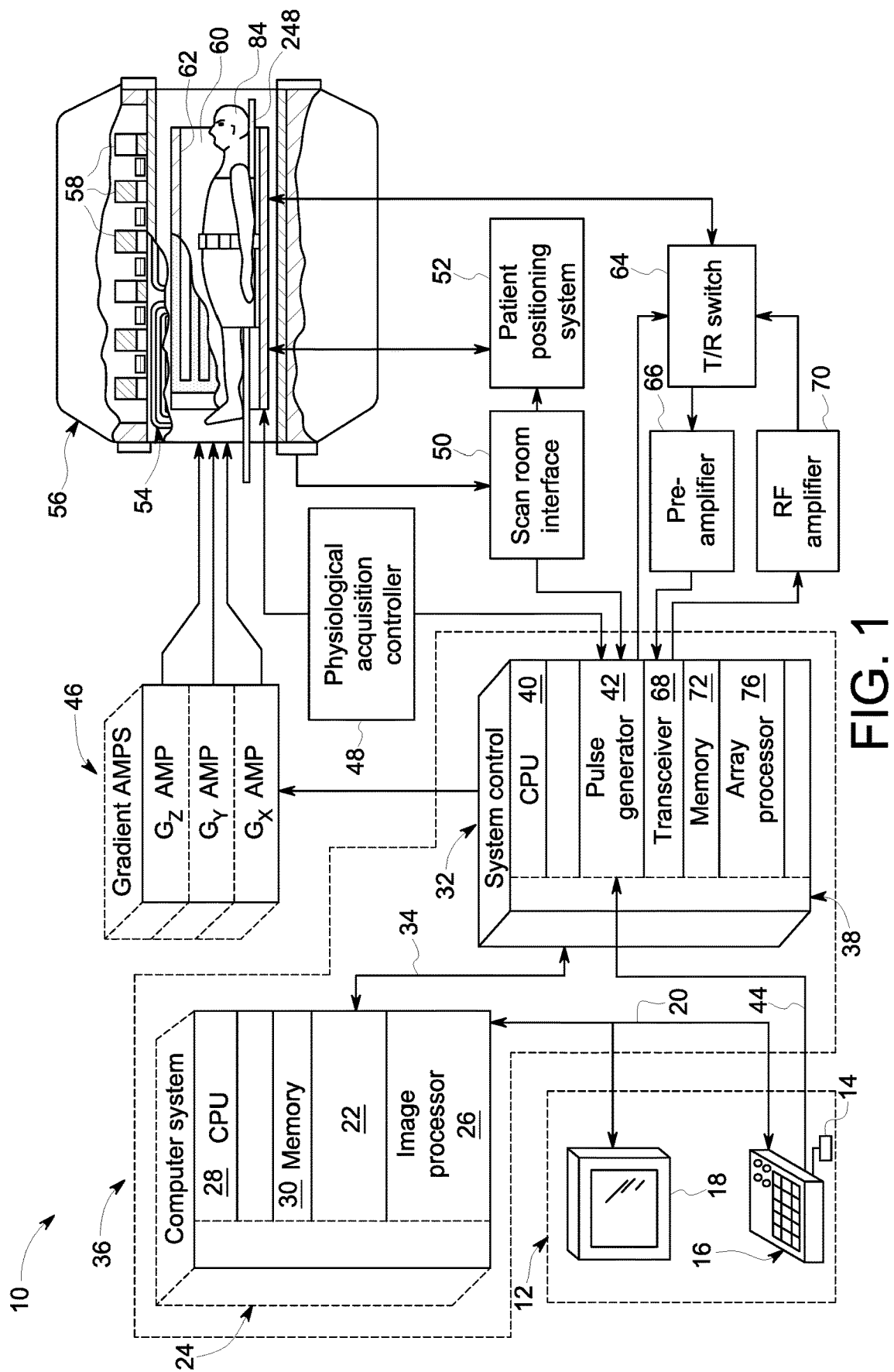
FIG. 1 is a block diagram of an MRI system, in accordance with an embodiment of the invention.

Referring now to FIG. 1, the major components of an MRI system 10 incorporating an embodiment of the invention are shown. Operation of the system 10 is controlled from the operator console 12, which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules, which communicate with each other through a backplane 24. These include an image processor module 26, a CPU module 28 and a memory module 30, which may include a frame buffer for storing image data arrays. The computer system 22 communicates with a separate system control or control unit 32 through a high-speed serial link 34. The input device 14 can include a mouse, joystick, keyboard, track ball, touch activated screen, light wand, voice control, or any similar or equivalent input device, and may be used for interactive geometry prescription. The computer system 22 and the MRI system control 32 collectively form an "MRI controller" 36.

The MRI system control 32 includes a set of modules connected together by a backplane 38. These include a CPU module 40 and a pulse generator module 42, which connects to the operator console 12 through a serial link 44. It is through link 44 that the system control 32 receives commands from the operator to indicate the scan sequence that is to be performed. The pulse generator module 42 operates the system components to execute the desired scan sequence and produces data which indicates the timing, strength and shape of the RF pulses produced, and the timing and length of the data acquisition window. The pulse generator module 42 connects to a set of gradient amplifiers 46, to indicate the timing and shape of the gradient pulses that are produced during the scan. The pulse generator module 42 can also receive patient data from a physiological acquisition controller 48 that receives signals from a number of different sensors connected to the patient, such as ECG signals from electrodes attached to the patient. And finally, the pulse generator module 42 connects to a scan room interface circuit 50, which receives signals from various sensors associated with the condition of the patient and the magnet system. It is also through the scan room interface circuit 50 that a patient positioning system 52 receives commands to move the patient to the desired position for the scan.

The pulse generator module 42 operates the gradient amplifiers 46 to achieve desired timing and shape of the gradient pulses that are produced during the scan. The gradient waveforms produced by the pulse generator module 42 are applied to the gradient amplifier system 46 having Gx, Gy, and Gz amplifiers. Each gradient amplifier excites a corresponding physical gradient coil in a gradient coil assembly, generally designated 54, to produce the magnetic field gradients used for spatially encoding acquired signals. The gradient coil assembly 54 forms part of a magnet assembly 56, which also includes a polarizing magnet 58 (which in operation, provides a homogenous longitudinal magnetic field Bo throughout a target volume 60 that is enclosed by the magnet assembly 56) and a whole-body (transmit and receive) RF coil 62 (which, in operation, provides a transverse magnetic field Bi that is generally perpendicular to Bo throughout the target volume 60).

The resulting signals emitted by the excited nuclei in the patient may be sensed by the same RF coil 62 and coupled through the transmit/receive switch 64 to a preamplifier 66. The amplifier MR signals are demodulated, filtered, and digitized in the receiver section of a transceiver 68. The transmit/receive switch 64 is controlled by a signal from the pulse generator module 42 to electrically connect an RF amplifier 70 to the RF coil 62 during the transmit mode and to connect the preamplifier 66 to the RF coil 62 during the receive mode. The transmit/receive switch 64 can also enable a separate RF coil (for example, a surface coil) to be used in either transmit or receive mode.

The MR signals picked up by the RF coil 62 are digitized by the transceiver module 68 and transferred to a memory module 72 in the system control 32. A scan is complete when an array of raw k-space data has been acquired in the memory module 72. This raw k-space data/datum is rearranged into separate k-space data arrays for each image to be reconstructed, and each of these is input to an array processor 76 which operates to Fourier transform the data into an array of image data. This image data is conveyed through the serial link 34 to the computer system 22 where it is stored in memory 30. In response to commands received from the operator console 12, this image data may be archived in long-term storage or it may be further processed by the image processor 26 and conveyed to the operator console 12 and presented on the display 18.

Figure 2:
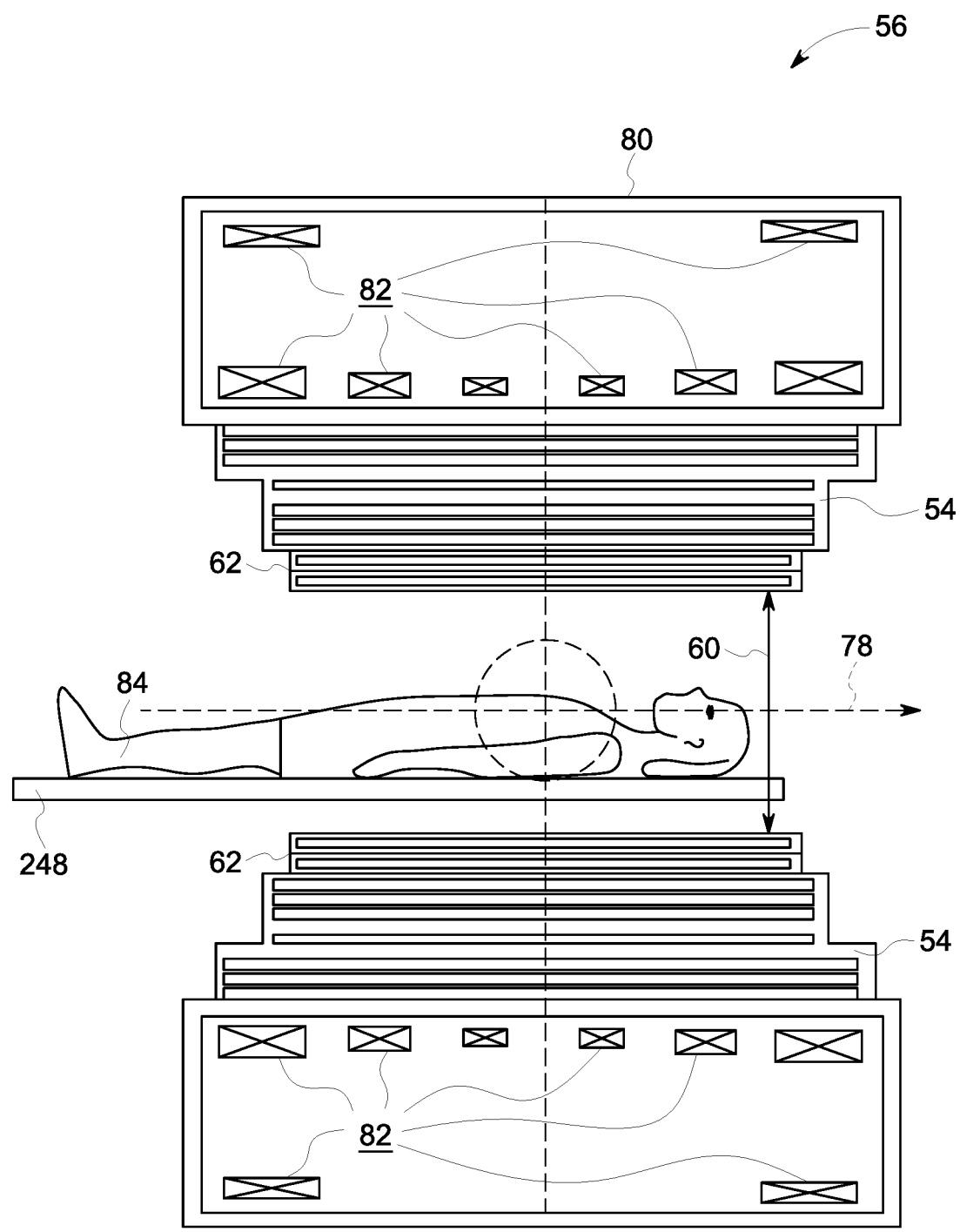
FIG. 2 is a schematic cross-sectional view of a magnet assembly of the MRI system of FIG. 1, in accordance with an embodiment of the invention.

As illustrated in FIG. 2, a schematic side elevation view of the magnet assembly 56 is shown in accordance with an embodiment of the invention. The magnet assembly 56 is cylindrical in shape having a center axis 78. The magnet assembly 56 includes a cryostat 80 and one or more radially aligned longitudinally spaced apart superconductive coils 82 that form the polarizing magnet 58. The superconductive coils 82 are capable of carrying large electrical currents and are designed to create the Bo field within the patient/target volume 60. As will be appreciated, the magnet assembly 56 may further include both a terminal shield and a vacuum vessel (not shown) surrounding the cryostat 80 in order to help insulate the cryostat 80 from heat generated by the rest of the MRI system 10 (FIG. 1). The magnet assembly 56 may still further include other elements such as covers, supports, suspension members, end caps, brackets, etc. (not shown). While the embodiment of the magnet assembly 56 shown in FIGS. 1 and 2 utilizes a cylindrical topology, it should be understood that topologies other than cylindrical may be used. For example, a flat geometry in a split-open MRI system may also utilize embodiments of the invention described below. As further shown in FIG. 2, a patient/imaged subject 84 is inserted into the magnet assembly 56.

Figure 4:
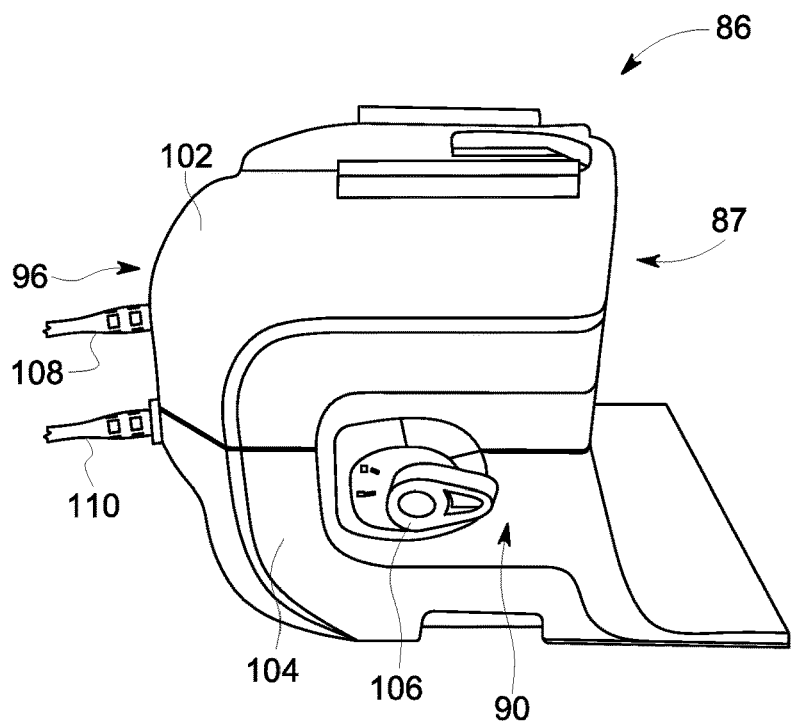
FIG. 4 is a perspective view of the right side of the RF head coil of FIG. 3, in accordance with an embodiment of the invention.
Figure 5:
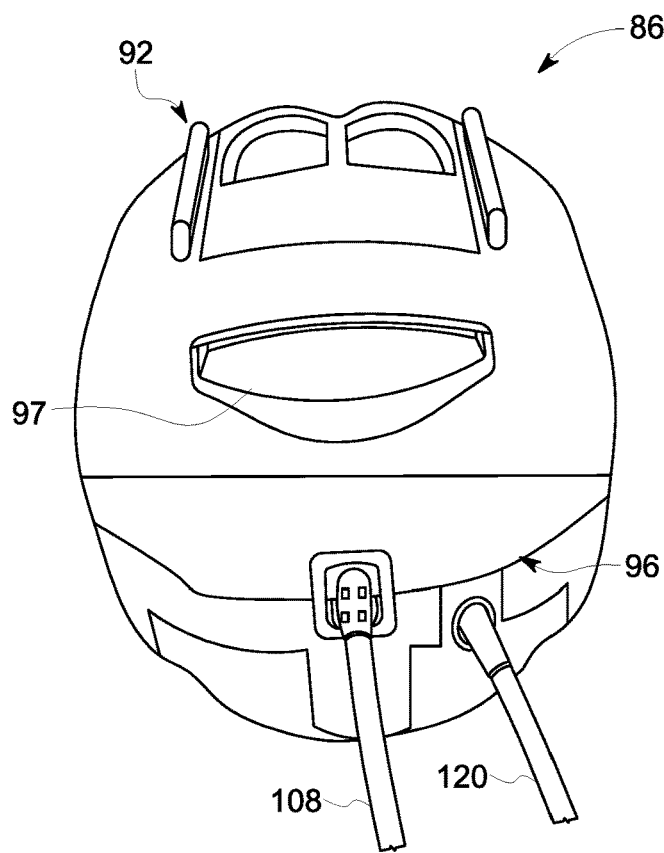
FIG. 5 is a perspective view of the top and front sides of the RF head coil of FIG. 3, in accordance with an embodiment of the invention.

Turning now to FIGS. 3 and 4, in embodiments the MRI system 10 may further include an RF head coil 86. The RF head coil 86 has a body 87 with a left side 88 (FIG. 3), a right side 90 (FIG. 4), a front side 92 (FIGS. 5, and 8-9), a back side 94 (FIG. 10), a top side 96 (FIGS. 4 and 5) which may include an integrated handle 97, a bottom side 98 (FIGS. 3 and 6-7), and an interior imaging cavity 100 (FIGS. 3 and 6-7) defined by one or more of the sides 88, 90, 92, 94, 96, and/or 98 and configured to contain the patient's 84 head. As shown in FIGS. 3 and 4, the RF head coil 86 is shaped to contain the head of the patient 84, e.g., the RF head coil 86 may be shaped like a helmet. Accordingly, in embodiments, the RF head coil 86 may include an anterior portion 102 (best seen in FIG. 11) and a posterior portion 104 (best seen in FIG. 12) that selectively interlock with one another so as to form/define the imaging cavity 100. In embodiments, the RF head coil 86 may further include one or more locking mechanisms 106 that selectively lock the anterior portion 102 to the anterior portion 104. As will be appreciated, in embodiments, the RF head coil 86 may receive and/or transmit radio frequencies into the patient/subject 84 being imaged, i.e., the RF head coil 86 may work in conjunction with, or separately from, the RF coil 62. Accordingly, in embodiments, the RF head coil 86 may include one or more cables 108 and 110 that electronically connect the RF head coil 86 to the transmit/receive switch 64.

Turning now to FIG. 11, the anterior portion 102 is configured to fit over the face of the head of the patient 84. Accordingly, in embodiments, the anterior portion 102 may include eye openings 112 and 114. In embodiments, the anterior portion 102 may further include a nose bridge 116 disposed between the eye openings 112 and 114.

As shown in FIG. 8, in embodiments, the anterior portion 102 may further include one or more mounting rails 118 disposed on front side 92 for mounting one or more devices, e.g., mirrors, Virtual Reality ("VR") and/or fMRI goggles, medical devices, etc., to the RF head coil 86. In embodiments, the mounting rails 118 may be round, square, and/or of any other appropriate design that allows goggles and/or other medical devise to selectively slide on and off of the RF head coil 86.

As further shown in FIG. 8 and in FIG. 9, in embodiments, the eye openings 112 and 114 may have a horizontal length 120 of about 75 mm and a vertical length 122 of about 90 mm, and the nose bridge 116 may have a width 124 of about 10 mm. Accordingly, in embodiments, the eye openings 112 and 114 may have a mean interpapillary distance ("IPD") 126 of about 55 mm and a SI that can accommodate from about 5% of the U.S. female population to about 99% of the U.S. male population, and an IPD 128 between about 45 mm to about 55 mm when goggles are mounted to the rails 118. As used herein, the term "IPD" refers to the distance between the centers of the patient's 84 pupils which affects the stereo separation of two images (one from each eye) which are combined by the brain to produce stereo perception. As such, in embodiments, the eye openings 112 and 114 may be ergonomically shaped having a horizontal length 120 of about 195 mm, a vertical length 122 of about 90 mm, and a nose bridge width 124 of about 15 mm, which may provide for a minimum IPD 128 of about 55 mm for a pair of goggles mounted to the rails 118 having about 40 mm diameter goggles, and a minimum IPD 128 of about 50 mm for mounted goggles having a diameter of about 35 mm. Thus, as will be appreciated, in embodiments, the eye openings 112 and 114 are sized so as to fit a wide variety of facial features, e.g., eye spacing/IPD, for use with and without goggles mounted to the rails 118.

Moving now to FIG. 12, in embodiments, the posterior portion 104 may include an extended lip/flange 130 that extends below the base of the patient's 84 brain stem 131 (best seen in FIG. 27) when the patient's 84 head is in the RF head coil 86. For example, in embodiments, the extended lip 130 may be sized so as to extend in a direction from the brain stem 131 along the patient's 84 spine to at least the fourth cervical ("C4") vertebra 133 (best seen in FIG. 27). In embodiments, the extended lip 130 may extend a distance that covers the C4 vertebra 133 of at least 95% of the U.S. male population. As will be explained in greater detail below, in embodiments, the RF head coil 86 may include coil elements within the extended lip 130 so as to provide for MRI image coverage/field of view that encompasses the patient's 84 head and the C4 vertebra, e.g., the RF head coil 86 may have a field of view extending at least about 34 cm. In other words, the body 87 of the RF head coil 86 may be operative to be disposed on and/or over a head of the patient 84 (FIG. 2) so that the extended lip 130 receives at least some of, e.g., portions/components, of the MR signal which are emitted by/from a region 135 (best seen in FIG. 27) disposed between the brain stem 131 and up to the C4 133 vertebra. It will be understood, however, that in embodiments, the length/size of the extended lip 130 may vary such that the length of the region 135 varies, e.g., the extended lip 130 may cover more or fewer vertebra than the C4 vertebra 133. Further, as will be appreciated, in embodiments, the extended lip 130 may be integrated into the posterior portion 104 (as shown in FIGS. 3 and 4) and/or may be separate from but selectively attachable to the posterior portion 104 at a joint/connection site (represented as dashed line 137 in FIGS. 19 and 20) via one or more fasteners 139 (FIGS. 19 and 20), e.g., matting slots, magnets, and/or other suitable devices for securing the extended lip 130 to the posterior portion 104.

Referring now to FIGS. 11 and 12, in embodiments, the locking mechanism 106 includes a catcher subassembly 132 (FIG. 11) and a locking subassembly 134 (FIG. 12), and as stated above, serves to selectively lock the anterior portion 102 to the posterior portion 104. While the accompanying figures depict the catcher subassembly 132 and the locking subassembly 134 disposed/integrated into the anterior portion 102 and the posterior portion 104, respectively, it will be understood that, in other embodiments, the catcher subassembly 132 and the locking subassembly 134 may be disposed/integrated into the posterior portion 104 and the anterior portion 102, respectively. As shown in FIGS. 13 and 14, in embodiments, the locking subassembly 134 includes a cover 136, a hook 138, and a handle 140. In embodiments, the hook 138 may be disposed on a hook subassembly 142 that is mounted to the posterior portion 104 such that the hook subassembly 142 is selectively rotatable along a horizontal axis 144 that runs from the left side 88 to the right side 90 of the RF head coil 86. As further shown in FIGS. 13 and 14, the cover 136 fits over the hook subassembly 142 and includes openings 146. The handle 140 is disposed against the cover 136 opposite the hook subassembly 142 such that the handle 140 mechanically connects with the hook subassembly 142 via one or more pins 148 that pass through the openings 146. In embodiments, the locking subassembly 134 may further include a handle cover 149 disposed against the handle 140 opposite the cover 136.

Accordingly, in embodiments, the locking mechanism 106 may selectively lock the anterior portion 102 to the posterior portion 104 via rotating the handle 140 clockwise along the horizontal axis 144, which in turn rotates the hook 138 such that the hook 138 is received by/mates with the catcher subassembly 132, i.e., the locking mechanism 106 is in a LOCKED position/state when the hook 138 is in/received by the catcher subassembly 132. The term "lock," as used herein with respect to the locking of the anterior portion 102 to the posterior portion 104 means that the anterior portion 102 is temporarily joined/held in place against the posterior portion 104 such that the anterior portion 102 is not readily separable from the posterior portion 104. Accordingly, the anterior portion 102 may be selectively unlocked from the posterior portion 104 by rotating the handle 140 counterclockwise along the horizontal axis 144, which in turn rotates the hook 138 such that the hook 138 is released/removed from the catcher subassembly 132, i.e., the locking mechanism 106 is in an UNLOCKED position/state when the hook 138 is free of the catcher subassembly 132. The term "unlock," as used herein with respect to the unlocking of the anterior portion 102 from the posterior portion 104 means that the anterior portion 102 is freely moveable with respect to the posterior portion 104 such that the anterior portion 102 is separable from the posterior portion 104.

It will be understood that in other embodiments, the anterior portion 102 may be selectively locked and unlocked to and from the posterior portion 104 by rotating the handle 140 counterclockwise and clockwise, respectively. Further, in embodiments, the degree of rotation of the hook 138 and/or the handle 140 about the horizontal axis 144 may be about thirty (30°) degrees. Further still, in embodiments, the hook 138 may be curved such that varying the degree of rotation of the hook 138 and/or handle 140 varies the tightness of the locking action, i.e., the strength of the force provided by the locking mechanism 106 that pulls the anterior portion 102 and the posterior portion 104 together. As will be appreciated, by locking and unlocking the anterior portion 102 to and from the posterior portion 104 via a rotation action, embodiments of the locking mechanism 106 provide for noiseless and/or near noiseless mechanism for securing and releasing the anterior portion 102 from the anterior portion 104. As will be appreciated, the various components of the locking mechanism 106, to include the hook 138, handle 140, hook subassembly 142, and/or cover 136 may be made of plastic and/or other lightweight materials, and may be additively manufactured, i.e., three dimensional ("3D") printed.

Accordingly, in order to provide tactile feedback to the patient 84 that the locking mechanism 106 has been rotated from a locked to an unlocked position, or vice versa, the locking subassembly 134 may further include a spring/plunger "bullet" 150. As will be appreciated, in embodiments, the spring bullet 150 may compress, decompress, and/or execute another type of movement, as the handle 140 is rotated about the axis 144 such that the spring bullet 150 generates vibrations which the patient 84 can sense, and in some embodiments, hear. As will be appreciated, the spring bullet 150 may be made of plastic and/or other lightweight material, and may also be additively manufactured. As further shown in FIG. 14, embodiments of the locking subassembly 134 may further include a flexible tongue shaped feature that also facilitates tactile feedback to the patient 84.

As will be further appreciated, in embodiments, the RF head coil 86 may include a single locking mechanism 106 on a single side 88, 90, 92, 94, 96, and/or 98. In other embodiments, the RF head coil 86 may include two or more locking mechanism 106 on multiple sides 88, 90, 92, 94, 96, and/or 98. In embodiments wherein the RF head coil 86 includes two or more locking mechanism 106, the locking and unlocking movements, e.g., the rotation of the hooks 138 and/or the handles 140, may be independent and/or dependent on each other. For example, locking/unlocking a locking mechanism 106 disposed on the left side 88 of the RF head coil 86 may lock/unlock a locking mechanism 106 disposed on the right side 90 of the RF head coil 86. In other embodiments, however, the hook 138 and handle 140 of a locking mechanisms 106 disposed on the left side 88 of the RF head coil 86 may be rotated independently of the hook 138 and the handle 140 of a locking mechanism 106 disposed on the right side 90 of the RF head coil 86.

Figure 6:
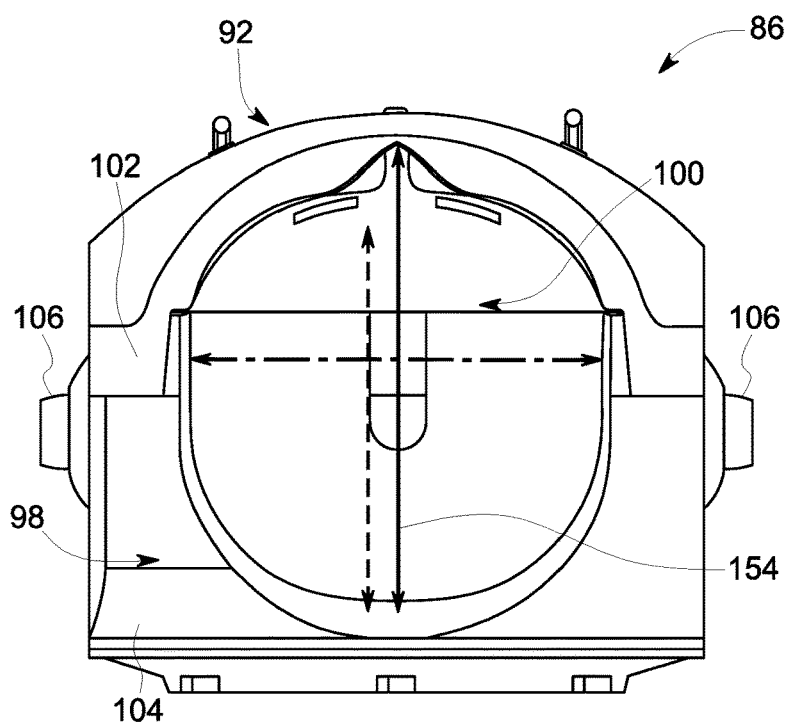
FIG. 6 is a view of the bottom side of the RF head coil of FIG. 3, in accordance with an embodiment of the invention.

Turning now to FIGS. 3 and 15, in embodiments, the RF head coil 86 may further include a spacer 152 configured to be selectively disposed between the anterior portion 102 and the posterior portion 104 so as to extend the size of the imaging cavity 100. As shown in FIG. 15, the spacer 152 may be "U-shaped." For example, FIG. 6 depicts an embodiment of the RF head coil 86 wherein the spacer 152 (not shown in FIG. 6) is not disposed between the anterior portion 102 and the posterior portion 104 and the imaging cavity 100 has a length 154 of about 23 cm. By contrast, FIG. 7 depicts an embodiment of the RF head coil 86 wherein the spacer 152 is disposed between the anterior portion 102 and the posterior portion 104 such that the imaging cavity 100 has a length 154 of about 26 cm. A will be appreciated, while the anterior 102 and posterior 104 portions may be sized to accommodate the heads of 98% of the U.S. population/patients 84, with respect to the distance from the nose to the back of the head, the spacer 152 may be adjusted to accommodate patients 84 having heads in the $99^{th}$ percentile, with respect to the distance from the nose to the back of the head. Thus, embodiments of the RF head coil 86 provide for an imaging cavity 100 that can accommodate nearly 99.9% of the U.S. population, with respect to the width from the nose to the back of the head, without having to oversize the interior cavity, which in turn reduces the effectiveness of the RF head coil 86 to transmit and receive the RF signals to and from the patient's 84 head.

As will be further appreciated, in order to stabilize a patient's 84 head within the imaging cavity 100, the RF head coil 86 may include one or more pads, e.g., head pads 156 (FIG. 16) and/or wedge pads 158 (FIG. 17) and 160 (FIG. 18). For example, in embodiments, the head pad 156 may be placed within the imaging cavity 100 against the anterior portion 104. The patient 84 may then place/lay their head on the head pad 156 such that the head pad 156 raises the patient's 84 head within the imaging cavity 100, e.g., spaces the patient's 84 head away from the anterior portion 104 and towards the center of the imaging cavity 100. The wedge pads 158 and/or 160 may then be used to immobilize the patient's 84 head within the imaging cavity 100. Once the patient's head has been raised and/or immobilized by the pads 156, 158, and/or 160, the anterior portion 102 may then be placed over the patient's 84 head and secured/locked to the posterior portion 104. As will be appreciated, in embodiments, the head pad 156 may have a thickness of about 15 mm to about 45 mm, and in some embodiments, may be about 30 mm. In embodiments, the head pad 156 may have an extended shoulder area 162 that may in turn form part of a KHNU pad design. As shown in FIG. 17, in embodiments, the wedge pads 158 may be generally rectangular in shape with rounded edges. In such embodiments, the wedge pads 158 may have a width of about 10 cm. As shown in FIG. 18, in embodiments, the wedge pads 160 may have a triangular shape. In such embodiments, the wedge pads 160 may have a width of 5 cm. In embodiments, the pads 156, 158, and/or 160 may include a RD welded healthcare fabric skin with an open cell foam core. Thus, as will be appreciated, in embodiments, the pads 156, 158, and/or 160 may provide for both the positioning of the patient's 84 head within the imaging cavity 100 and/or improve patient 84 comfort. As such, in embodiments, the pads 156, 158, and/or 160 may have thicknesses of about 1.5 cm, 3 cm, and/or 4.5 cm.

Referring to FIGS. 19 and 20, in embodiments, the RF head coil 86 may include a mirror assembly 164 that provides the patient 84 a front view 166 and/or a rear view 168, which in embodiments, may allow the patient 84 to view a relaxing image on a screen and/or to view the operator of the MRI system 10. For example, and as shown in FIGS. 21-23, in embodiments, the mirror assembly 164 includes one or more mirrors 170, 172, 174 disposed in a v-shaped holder 176 rotatably mounted to a u-shaped bracket 178. The u-shaped bracket 178 includes two frame legs 180 that slideably mount to the mounting rails 118. In embodiments, the mirror assembly 164 further includes a u-shaped cover 182 that fits over the u-shaped bracket 178, and/or a mirror lock 184 which, as explained below, provides for the ability to lock the position of the v-shaped holder 176 with respect to the u-shaped bracket 178.

As shown in FIGS. 21-23, in embodiments, the v-shaped holder 176 has two legs 186 and 188, wherein a first mirror 170 is disposed on a surface defined by the first leg 186 such that the first mirror 170 faces the second leg 188. In such embodiments, a second 172 and a third 174 mirror may be disposed on opposite surfaces defined by the second leg 188 of the v-shaped holder 176 such that the second mirror 172 faces the first leg 186 so that the first 170 and the second 172 mirrors are in optical communication. In embodiments, the v-shaped holder 176 may be mounted to the u-shaped bracket 178 at the intersection of the two legs 186 and 188, i.e., at the "v" of the v-shaped holder 176, such that the frame legs 180 extend down from the "v" of the v-shaped holder 176. In other words, the "v" of the v-shaped holder 176 is mounted within the "u" of the u-shaped bracket 178 such that the v-shaped holder 176 can rotate about an axis of rotation 190. In embodiments, the axis of rotation 90 is above the center of gravity of the mirror assembly 164. Further, in embodiments, the frame legs 180 may further include flexible clips 192 for connecting/mounting the mirror assembly 164 to the mounting rails 118.

Accordingly, in embodiments, after the patient's 84 head has been placed in the RF head coil 86 with the anterior portion 102 locked to the posterior portion 104, the mirror assembly 164 may be mounted via the frame legs 180 such that the flexible clips 192 mate with the mounting rails 118. The v-shaped holder 176 may then be rotated to one of a front view position (as shown in FIG. 21) or a rear view position (as shown in FIGS. 19, 20 and 23. As will be understood, in the front view position, the first mirror 170 is in optical communication with the second mirror 172 such that the second mirror 172 reflects a front view 166 to the first mirror 170 which in turn reflects the front view 166 towards the patient's 84 head. In such embodiments, the v-shaped holder 176 may be oriented such that the second leg 188 is parallel to the frame legs 180. As will be further understood, in the rear view position, the third mirror 174 reflects the rear view 168 towards the patient's head. In such embodiments, the v-shaped holder 176 may be oriented such that the first leg 186 is perpendicular to the frame legs 180. As will be also appreciated, the mirror assembly 164 may be slideably adjustable on the mounting rails 118 such that the mirror assembly 164 can be aligned with the eye openings 112 and 114 so that the first mirror 170 or the third mirror 174 optically communicates with the patient's 84 eyes when the v-shaped holder 176 is in the front view position or the rear view position, respectively. As will be understood, in embodiments, the radial distance between the front view position and the rear view position may be about 27-28° along the axis of rotation 190.

Further, as stated above, the mirror lock 184 provides for the ability to lock the position of the v-shaped holder 176 with respect to the u-shaped bracket 178, i.e., the mirror lock 184 locks the position of the mirrors 170, 172, 174. Accordingly, in embodiments, the mirror lock 184 may include spring action plungers 194 with matching holes 196. Further in embodiments, the first leg 186 and the second leg 188 may be radially spaced apart on the axis of rotation 190 by about 45°.

Moving now to FIGS. 24 and 25, in embodiments, the anterior portion 102 may include an anterior snap-fit bracket shell 198 disposed within the anterior portion 102, and the posterior portion 104 may include a posterior snap-fit bracket shell 200 disposed within the posterior portion 104. As will be appreciated, in embodiments, the anterior snap-fit bracket shell 198 and the posterior snap-fit bracket shell 200 are shaped to conform to the anterior 102 and posterior 104 portions, respectively, and serve as a support structures to which artwork and feedboards 202, i.e., electronics that form coil elements (best seen in FIGS. 26-29), may be mounted to. For example, in embodiments the anterior 198 and the posterior 200 snap-fit bracket shells may be additively printed apart from the anterior 102 and the posterior 104 portions. The artwork and/or feedboards 202 may then be mounted to the anterior 198 and the posterior 200 snap-fit bracket shells, which are then in turn mounted into the anterior 102 and the posterior 104 sections, respectively. For example, FIG. 24 depicts the front side 204 of the anterior snap-fit bracket shell 198 which aligns, i.e., faces in the same direction, with the front side 92 of the RF head coil 86. As shown in FIG. 24, the front side 204 of the anterior snap-fit bracket shell 198 has a convex shape such that the back side (not shown and opposite of the front side 204) forms around the face of the patient 84. Similarly, FIG. 25 depicts the back side 206 of the posterior snap-fit bracket shell 200 which aligns, i.e., faces in the same direction, with the back side 94 of the RF head coil 86. As shown in FIG. 25, the back side 206 of the posterior snap-fit bracket shell 200 also has a convex shape such that the front side (not shown and opposite the back side 206) forms around the back of the patient's 84 head. As such, the convex shape of the front 204 and back sides 206 of the anterior 198 and posterior 200 snap-fit bracket shells, respectively, provide for an improved method of installing the artwork and/or feedboards 202 into the anterior 102 and posterior 104 portions. As will be appreciated, in embodiments, the artwork and/or feedboards 202 may be mounted to the anterior 198 and posterior 200 snap-fit bracket shells via press-fit-snaps & o-rings.

Turning now to FIGS. 26-29, as stated above, the artwork and/or feedboards 202 (FIGS. 24 and 25) form coil elements generally designated 208 (for the anterior portion 102) and 210 (for the posterior portion). In embodiments, the body 87 and the extended lip 130 may collectively include forty-eight (48) coil elements. For example, as shown in FIG. 28, the anterior portion 102 may include sixteen (16) coil elements E1-E16 arranged, generally, into four rows 212, 214, 216, and 218. As will be understood, the coil elements E1-E16 may overlap one another. As shown in FIG. 29, the posterior portion 104 may include thirty-two (32) coil elements E1-E32 arranged, generally, into five rows 220, 222, 224, 226, and 228, with an additional row 230 formed by four (4) coil elements E29-E32 within the extended lip 130 that cover the C4 vertebra of the patient 84. As will be understood, the coil elements E1-E32 may overlap one another. In embodiments, the coil elements 208 and 210 may provide for a field of view ("FOV") of about 24 cm. As will be appreciated, the arrangement of the coil elements 208 and 210 disclosed herein provides for thicker imaging slices, higher signal to noise ratios, and higher/faster acceleration during HyperBand imaging by keeping a reduction factor of four (4) for patient's 84 having shorter than average necks or a reduction factor of five (5) for patient's 84 having average neck lengths or greater. As used herein, HyperBand imaging refers to an MR imaging method that provides for reduced scan times via simultaneous excitation of multiple slices at multiple locations which, in embodiments, may be combined with other MR imaging methods, e.g., parallel imaging, to facilitate higher acceleration reduction factors. As such, HyperBand imaging may improve a patient's 84 experiences by shortening breadth hold times, increase anatomy coverage, and provide for higher resolution image acquisitions.

Referring now to FIGS. 30 and 31, in embodiments, the RF head coil 86 may be configured to facilitate silent MR imaging which, as used herein, refers to an MR imaging/scanning method which attempts to reduce MR noise by mitigating and or eliminating the rapid switching of gradient coils 54. As will be appreciated, in embodiments, silent MR imaging reduces and/or eliminates mechanical vibration resulting from rapidly shifting the gradient coils, which in turn, mitigates/reduces noise generated during RF signal acquisition. As will be further appreciated, silent MR imaging acquires 3D MR data that yields isotropic resolution.

Accordingly, as silent MR imaging eliminates and/or mitigates rapid switching of the gradient coils 54, embodiments of the RF head coil 86 may be operative to switch from transmit mode to receive mode within microseconds so as to maximize the signal to noise ratio ("SNR") within the acquired images. For example, in embodiments, the coil elements 208 and/or 210 of the RF head coil 86 may include one or more micro-electro-mechanical ("MEM") switches 232. For example, in embodiments, the coil elements 208 and/or 210 may each include one or more single mem switches 234, 236 and/or one or more dual mem switches 238, 240. For example, in embodiments, with respect to the coil elements 208 of the anterior portion 102, coil elements E1-E13 and E16 may each include a single MEM switch 234, with coil elements E14 and E15 (which cover the eye openings 112 and 114) each including dual MEM switches 238. Similarly, in embodiments, with respect to the coil elements 210 in the posterior portion 104, coil elements E1-E28 may each include a single MEM switch 236 with coil elements E29-E32 (which cover the extended lip 130/ C4 vertebra of the patient 84) each including dual MEM switches 240.

Additionally, in embodiments, the RF head coil 86 may include one or more high Z preamplifiers 242 and one or more MEM drivers 244. As shown in FIG. 31, the high Z preamplifiers 242 and the MEM drivers 244 may be optimized to improve the switching time from receive mode to transmit mode of the RF head coil 86. For example, in embodiments, the RF head coil 86 may settle between about 90% to 110% of the steady state signal level within 20 usec of the rising edge of the RF enable signal. Further, in embodiments, the coil elements 208 in the anterior portion 102 and the coil elements 210 in the posterior portion 104 may be electrically independent of each other. In other words, in emblements the coil elements 208 may electrically communicate with the MRI controller 36 and/or the transmit/receive switch 64 via cable 108 (best seen in FIG. 4), and the coil elements 210 may electronically communicate with the MRI controller 36 and/or the transmit/receive switch 64 via cable 110 (best seen in FIG. 4). Thus, as will be appreciated, by utilizing separate cables 108 and 110 for the electronic communication to and from the anterior portion 102 and the posterior portion 104, embodiments of the invention provide for increased bandwidth, signaling speed, and reliability between the MRI controller 36, and/or transmit/receive switch 64, and the RF head coil 86.

Turning now to FIGS. 32-35, in embodiments, the RF head coil 86 may further include a table adapter 246 configured to support and/or retain the RF head coil 86 on the on a table 248 (best seen in FIGS. 1 and 2). As will be appreciated, the table adapter 246 provides for the RF head coil 86 to be utilized with MRI systems having tables that do not readily conform to the back side 94 of the RF head coil 86, and/or may provide for inclining/tilting of the RF head coil 86 as shown in FIG. 33. Accordingly, in embodiments, the table adapter 246 may include one or more connection sites 250 that pair with one or more corresponding connection sites 252 (FIG. 10) on the back side 94 of the RF head coil 86. In embodiments, the connection sites 250 and 252 form fasteners, e.g., pegs and holes, magnets, rails, etc.

Additionally, as will be appreciated, in embodiments, one or more of the various components of the RF head coil 86 disclosed herein, to include anterior 102 and posterior portions 104, as well as the mirror assembly 164 and table adapter 246, may be made of a copolyester material to include MXF121, X HC-6023-006-2, or modified versions thereof. As will be appreciated, in embodiments, the copolyester material may inherently act as a disinfectant and additionally be flame-retardant, e.g., a UL 94 V2 rating at 1.5 mm while meeting hospital environmentally preferable purchasing ("EPP") guidelines, e.g., made without bisphenol A ("BPA"), halogens, or ortho-phthalate plasticizers. Further, in embodiments, the copolyester material may have a proton signal compatible for use in the MRI system 10, i.e., the copolyester material may have low and/or no MRI visibility, and capable of withstanding a variety of environmental stresses to include exposure to a variety of cleaners and disinfectants typically used in a hospital, e.g., Quaternary Ammonium Chlorides, isopropyl alcohol, and bleach. For example, in embodiments, the copolyester material may have a specific gravity (ASTMD-792) between about 1.2 to about 1.305, a mold shrinkage (flow direction) (ASTM D-955) between about 0.005 to about 0.007, a mold shrinkage (traverse direction) (ASTM D-955) between about 0.0040 to about 0.007; a tensile strength at yield (ASTM D-638) between about 6000 psi to 9000 psi, an elongation at break (ASTM D-638) of between about 50% to about 75%, a flexural modulus (ASTM D-790) between about 200000 psi to about 330000 psi, a flexural yield (ASTM D-790) between about 10000 pst to about 11000 pst, a HDT at about 66 psi (ASTM D-648) between about 100.0° C. to about 140° C., a notched izod impact (ASTM D-256) between about 1.5 ft-lb/in to about 13 ft-lb/in, and a fame performance at about ⅛" and/or about 1/16" (internal) of about V-0.

As will be appreciated, forming one or more of the aforementioned components of the RF head coil 86 from a copolyester material reduces and/or eliminates cracking of the components as compared to traditional materials typically made from polycarbonates. Further, since many copolyesters have an injection molding shrink value similar to polycarbonate, the above mentioned RD head coil 86 components may be manufactured via the same and/or preexisting tooling and machinery used to manufacture traditional polycarbonates components.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a radio frequency head coil for a magnetic resonance imaging system is provided. The radio frequency head coil includes a body operative to be disposed on a head of a patient, and an extended lip disposed on the body and operative to receive a magnetic resonance signal. At least some of the magnetic resonance signal is emitted by a region of the patient disposed between a brain stem of the patient up to and including a vertebra of the patient. In certain embodiments, the vertebra is a C4 vertebra. In certain embodiments, the extended lip provides for a field of view extending at least about 34 cm from the brain stem in a direction towards the vertebra. In certain embodiments, the extended lip extends from the body in a direction towards the vertebra. In certain embodiments, the vertebra is a C4 vertebra and the extended lip extends at least to the vertebra. In certain embodiments, the extended lip is integrated into the body. In certain embodiments, the extended lip is selectively attachable to the body. In certain embodiments, the body and the extended lip collectively include at least forty-eight coil elements.

Other embodiments provide for a magnetic resonance imaging system. The magnetic resonance imaging system includes a magnet assembly operative to stimulate a patient such that the patient emits a magnetic resonance signal. The magnetic resonance imaging system further includes a radio frequency head coil operative to be disposed on a head of the patient and having an extended lip operative to receive the magnetic resonance signal. The magnetic resonance imaging system further includes a controller in electronic communication with the radio frequency head coil and operative to generate one or more images based at least in part on the magnetic resonance signal. At least some of the magnetic resonance signal is emitted by a region of the patient disposed between a brain stem of the patient up to and including a vertebra of the patient. In certain embodiments, the vertebra is a C4 vertebra. In certain embodiments, the extended lip provides for a field of view extending at least about 34 cm from the brain stem in a direction towards the vertebra. In certain embodiments, the extended lip extends from the body in a direction towards the vertebra. In certain embodiments, the vertebra is a C4 vertebra and the extended lip extends at least to the vertebra. In certain embodiments, the extended lip is integrated into the body. In certain embodiments, the extended lip is selectively attachable to the body. In certain embodiments, the radio frequency head coil includes at least forty-eight coil elements.

Yet still other embodiments provide for, a method of magnetic resonance imaging a patient. The method includes: stimulating a patient via a magnet assembly such that the patient emits a magnetic resonance signal; receiving the magnetic resonance signal via an extended lip of a radio frequency head coil disposed on a head of the patient; and generating one or more images based at least in part on the magnetic resonance signal via a controller in electronic communication with the radio frequency head coil. At least some of the magnetic resonance signal is emitted by a region of the patient disposed between a brain stem of the patient up to and including a vertebra of the patient. In certain embodiments, the vertebra is a C4 vertebra. In certain embodiments, the extended lip provides for a field of view extending at least about 34 cm from the brain stem in a direction towards the vertebra. In certain embodiments, the extended lip extends from a body of the radio frequency coil in a direction towards the vertebra. In certain embodiments, the vertebra is a C4 vertebra and the extended lip extends at least to the vertebra. In certain embodiments, the extended lip is integrated into a body of the radio frequency head coil. In certain embodiments, the extended lip is selectively attachable to a body of the radio frequency head coil. In certain embodiments, the radio frequency head coil includes at least forty-eight coil elements.

Accordingly, by including an extended section within a RF coil, some embodiments of the invention provide for an MRI system that capture/depict a patient's head along with portions of the patient's spine, up to the C4 vertebra, within the same image. Thus, some embodiments of the present invention provide for an MRI system, and/or a RF head coil, having an improved field of view over traditional MRI systems, and/or RF head coils.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A radio frequency (RF) head coil for a magnetic resonance imaging (MRI) system comprising:
   a body operative to be disposed on a head of a patient;
   an extended lip disposed on the body and operative to receive a magnetic resonance signal;
   wherein at least some of the magnetic resonance signal is emitted by a region of the patient disposed between a brain stem of the patient up to and including a vertebra of the patient; and
   wherein the body comprises a posterior portion operative to receive the head of the patient and an anterior portion operative to be disposed on the head of the patient opposite the posterior portion so as to fit over a face of the patient;
   wherein the posterior portion and the anterior portion selectively interlock with one another to form an interior imaging cavity; and
   wherein the RF head coil includes a spacer configured to be selectively disposed between the anterior portion and the posterior portion so as to extend the size of the imaging cavity.

2. The radio frequency head coil of claim 1, wherein the vertebra is a C4 vertebra.

3. The radio frequency head coil of claim 1, wherein the extended lip provides for a field of view extending at least about 34 cm from the brain stem in a direction towards the vertebra when the body is disposed on the head of the patient.

4. The radio frequency head coil of claim 1, wherein the extended lip extends from the body in a direction towards the vertebra when the body is disposed on the head of the patient.

5. The radio frequency head coil of claim 4, wherein the vertebra is a C4 vertebra and the extended lip extends at least to the vertebra when the body is disposed on the head of the patient.

6. The radio frequency head coil of claim 1, wherein the extended lip is integrated into the body.

7. The radio frequency head coil of claim 1, wherein the extended lip is selectively attachable to the body.

8. The radio frequency head coil of claim 1, wherein the body and the extended lip collectively include at least forty-eight coil elements.

9. The radio frequency head coil of claim 8, wherein each of the at least forty-eight coil elements include one or more micro-electro-mechanical ("MEM") switches.

10. The radio frequency head coil of claim 1, wherein the anterior portion further includes one or more mounting rails disposed on a front side for mounting one or more devices.

11. The radio frequency head coil of claim 10 further comprising a mirror assembly that provides the patient a front view and a rear view.

12. The radio frequency head coil of claim 11, wherein the mirror assembly includes a first mirror and a second mirror disposed in a v-shaped holder rotatably mounted to a u-shaped bracket.

13. The radio frequency head coil of claim 12, wherein the u-shaped bracket includes at least two frame legs that slideably mount to the one or more mounting rails.

14. The radio frequency head coil of claim 1, wherein the extended lip is sized so as to extend in a direction from the brain stem along the patient's spine to at least a fourth cervical ("C4") vertebra.

15. The radio frequency head coil of claim 1 further comprising a table adapter configured to retain the RF head coil on a table of the MIII system.

16. The radio frequency head coil of claim 1, wherein the spacer has a U-shaped structure.

17. A magnetic resonance imaging system comprising:
   a magnet assembly operative to stimulate a patient such that the patient emits a magnetic resonance signal;
   a radio frequency (RF) head coil having a body operative to be disposed on a head of the patient and having an extended lip operative to receive the magnetic resonance signal;
   a controller in electronic communication with the radio frequency head coil and operative to generate one or more images based at least in part on the magnetic resonance signal;
   wherein at least some of the magnetic resonance signal is emitted by a region of the patient disposed between a brain stem of the patient up to and including a vertebra of the patient; and
   wherein the body comprises a posterior portion operative to receive the head of the patient and an anterior portion operative to be disposed on the head of the patient opposite the posterior portion so as to fit over a face of the patient;
   wherein the posterior portion and the anterior portion selectively interlock with one another to form an interior imaging cavity; and
   wherein the RF head coil includes a spacer configured to be selectively disposed between the anterior portion and the posterior portion so as to extend the size of the imaging cavity.

18. The magnetic resonance imaging system of claim 17, wherein the vertebra is a C4 vertebra.

19. The magnetic resonance imaging system of claim 17, wherein the extended lip provides for a field of view extending at least about 34 cm from the brain stem in a direction towards the vertebra when the body is disposed on the head of the patient.

20. The magnetic resonance imaging system of claim 17, wherein the extended lip extends from the body of the radio frequency head coil in a direction towards the vertebra the body is disposed on the head of the patient.

21. The magnetic resonance imaging system of claim 20, wherein the vertebra is a C4 vertebra and the extended lip extends at least to the vertebra when the body is disposed on the head of the patient.

22. The magnetic resonance imaging system of claim 17, wherein the extended lip is integrated into the body of the radio frequency head coil.

23. The magnetic resonance imaging system of claim 17, wherein the extended lip is selectively attachable to the body of the radio frequency head coil.

24. The magnetic resonance imaging system of claim 17, wherein the radio frequency head coil includes at least forty-eight coil elements.

25. A method of magnetic resonance imaging a patient comprising:
   stimulating a patient via a magnet assembly such that the patient emits a magnetic resonance signal;
   receiving the magnetic resonance signal via an extended lip of a radio frequency (RF) head coil having a body which is disposed on a head of the patient;
   generating one or more images based at least in part on the magnetic resonance signal via a controller in electronic communication with the radio frequency head coil;

wherein at least some of the magnetic resonance signal is emitted by a region of the patient disposed between a brain stem of the patient up to and including a vertebra of the patient; and wherein the body comprises a posterior portion operative to receive the head of the patient and an anterior portion operative to be disposed on the head of the patient opposite the posterior portion so as to fit over a face of the patient;

wherein the posterior portion and the anterior portion selectively interlock with one another to form an interior imaging cavity; and wherein the RF head coil includes a spacer configured to be selectively disposed between the anterior portion and the posterior portion so as to extend the size of the imaging cavity.

26. The method of claim 25, wherein the vertebra is a C4 vertebra.

27. The method of claim 25, wherein the extended lip extends from the body of the radio frequency head coil in a direction towards the vertebra.

28. The method of claim 27 wherein the radio frequency head coil includes at least forty-eight coil elements.

* * * * *